(12) United States Patent
Kolmar et al.

(10) Patent No.: US 8,258,258 B2
(45) Date of Patent: Sep. 4, 2012

(54) DIMERIC OR MULTIMERIC MICROPROTEINS

(75) Inventors: Harald Kolmar, Muhltal (DE); Ernst Boehnlein, Langenfeld (DE); Alexander Wentzel, Trondheim (NO); Hans-Ulrich Schmoldt, Darmstadt (DE)

(73) Assignee: BioNTech AG (DE)

( * ) Notice: Subject to any disclaimer, the term of this patent is extended or adjusted under 35 U.S.C. 154(b) by 997 days.

(21) Appl. No.: 11/886,007

(22) PCT Filed: Mar. 9, 2006

(86) PCT No.: PCT/EP2006/002188
§ 371 (c)(1),
(2), (4) Date: Jul. 14, 2008

(87) PCT Pub. No.: WO2006/094813
PCT Pub. Date: Sep. 14, 2006

(65) Prior Publication Data
US 2009/0156476 A1    Jun. 18, 2009

(30) Foreign Application Priority Data

Mar. 10, 2005  (EP) .................................. 05005292

(51) Int. Cl.
*A61K 38/16*  (2006.01)

(52) U.S. Cl. ......... 530/323; 530/317; 530/324; 514/7.8; 514/21.1; 514/21.3; 514/21.2

(58) Field of Classification Search ......................... None
See application file for complete search history.

(56) References Cited

U.S. PATENT DOCUMENTS

2003/0059877 A1 * 3/2003 Mosselman et al. ......... 435/69.1

FOREIGN PATENT DOCUMENTS

| WO | 96/40750 A | 9/1996 |
|----|------------|--------|
| WO | 00/58473 A | 10/2000 |
| WO | 01/85930 A | 11/2001 |
| WO | 02/098902 A | 12/2002 |
| WO | 2006/032436 A | 3/2006 |

OTHER PUBLICATIONS

Willuhn et al., "cDNA cloning of a Cadmium-inducible mRNA encoding a novel cysteine-rich, non-metallothionein 25-KDa protein in an Enchytraeid earthworm", The Journal of Biological Chemistry, vol. 269, No. 14, pp. 24688-24691, 1994.
Deyev et al., "Design of multivalent complexes using barnase-barstar module", Nature Biotechnology, vol. 21, No. 12, pp. 1486-1492, 2003.
Schmoldt et al., "A fusion protein system for the recombinant production of short disulfide bond rich cystine knot peptides using barnase as a purification handle", Protein Expression and Purification, vol. 39, No. 1, pp. 82-89, 2005.
Niemann et al., "Barnase fusion as a tool to determine the crystal structure of the small disulfide-rich protein McoEeTI", Journal of Molecular Biology, vol. 356, No. 1, pp. 1-8, 2006.
Gaertner et al., "Construction of protein analogues by site specific condensation of unprotected fragments", Bioconjugate Chemistry, vol. 3, No. 3, pp. 262-268, 1992.
Majerle et al., "Production of stable isotope enriched antimicrobial peptides in *Escherichia coli*: An application to the production of a 15N-enriched fragment of lactoferrin", Journal of Biomolecular NMR, vol. 18, pp. 145-151, 2000.
Te Piao King et al., "Preparation of protein conjugates via intermolecular hydrazone linkage", Biochemistry, vol. 25, pp. 5774-5779, 1986.
Rose et al., "Natural peptides as building blocks for the synthesis of large protein-like molecules with hydrazone and oxime linkages", Bioconjugate Chemistry, vol. 7, pp. 552-556, 1996.

* cited by examiner

*Primary Examiner* — Christina Bradley
(74) *Attorney, Agent, or Firm* — McAndrews, Held & Malloy, Ltd.

(57) ABSTRACT

Disclosed is a polypeptide comprising at least two microproteins, which preferably comprise an amino acid sequence having a specific binding activity to a target protein. Furthermore, disclosed are polynucleotides encoding such a polypeptide as well as pharmaceutical compositions and kits comprising said polypeptide or polynucleotide. Also disclosed herein are methods of treatments and second medical uses applying the disclosed polypeptide or polynucleotide. Additionally, the disclosure of the present application relates to a method for forming a covalent bond in a microprotein which can be used for producing the disclosed polypeptides.

18 Claims, 13 Drawing Sheets

DIMERIC OR MULTIMERIC MICROPROTEINS

Figure 1:
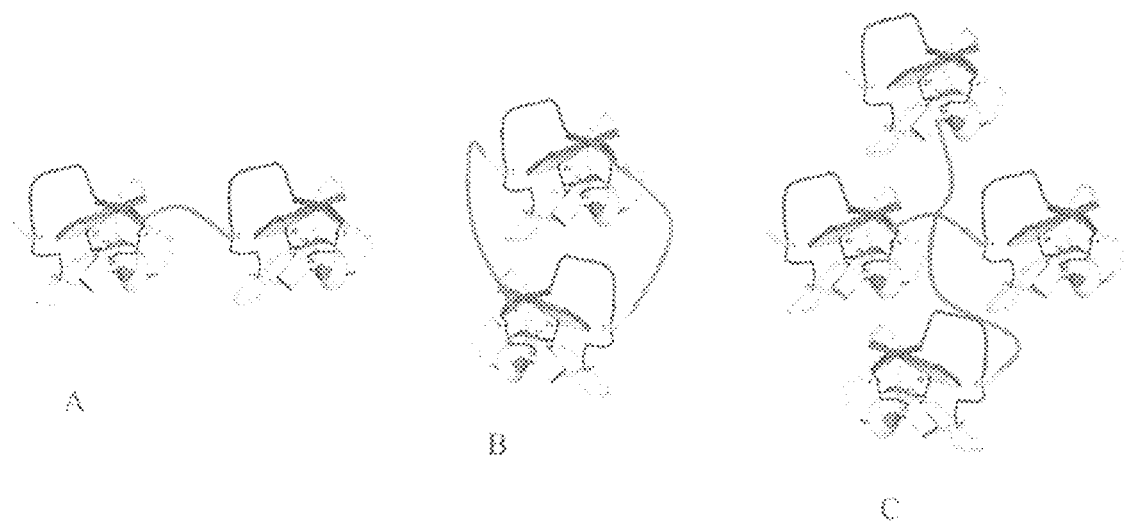

The present application is a National Phase of International Application No. PCT/EP2006/002188 filed Mar. 9, 2006, which claims priority to European Patent Application No. 05005292.7 filed Mar. 10, 2005. The contents of both applications are expressly incorporated herein by reference in their entireties.

The present invention refers to a polypeptide comprising at least two microproteins, which preferably comprise an amino acid sequence having a specific binding activity to a target protein. The present invention furthermore refers to polynucleotides encoding such polypeptides as well as to pharmaceutical compositions and kits comprising said polypeptide or polynucleotide. The present invention is also directed to methods of treatments and second medical uses applying the polypeptide or polynucleotide of the invention. The present invention additionally refers to a method for forming a covalent bond in a microprotein which can be used for producing the polypeptides of the invention.

The present invention relates to the field of peptides and peptide mimetics for use in therapy. In the prior art, it is an established approach to explore peptides and polypeptides, and analogous thereof, for therapeutic applications. Such approaches are in a major aspect based on attempts to modify protein-protein interactions which naturally occur in the body of a human or animal. In particular, it has been found that ligand-receptor interactions may be modulated by agonistic or antagonistic artificial ligand molecules. For example, upon dimerization of ligand molecules, dimeric membrane-bound receptors could be stimulated by binding of said ligand. This approach is based on investigations on cytokines and hormones many of which act as agonists by triggering signal transduction cascades. It has been observed that often signal transduction processes are initiated by bringing together two receptor molecules by the respective agonist. In many cases, the agonist is a dimer where each monomer binds a monomeric receptor molecule thereby activating the signal transduction process or a single monomer which contains two spatially distinct binding sites (Frank 2002, Grotzinger 2002, Mellado et al., 2001).

A well known example where activation of a cell surface receptor results from spatially connecting two receptor molecules by a receptor ligand is the Tpo/TpoR system (Dower et al., 1998; Geddis et al., 2002). Thrombopoietin (TPO) is a 332-amino acid glycosylated polypeptide which plays a key role in the regulation of megakaryocytopoiesis, the process in which platelets are produced from bone marrow megakaryocytes (Kuter et al., 1994, Kaushansky et al., 1994; Wendling et al., 1994, Sauvage et al., 1994). Thus, TPO has potential useful applications in both the diagnosis and the treatment of various hematological disorders, for example, diseases primarily due to platelet defects or thrombocytopenic conditions. A few years ago, the development of TPO peptide mimetics was reported (WO 96/40750, WO 98/25965, Cwirla et al., 1997). These peptides were designed to bind and activate the TpoR but have no sequence homology to the natural TPO. These molecules have been described to bind with high affinity to the TPO receptor (TPOR), act as TPOR agonists which can be further optimised by chemical cross-linking to form dimers that are as active as the natural cytokine TPO. A peptide sequence that has been shown to be highly active is the following: IEGPTLRQWLAARA (Cwirla et al., 1997). A peptide comprising this sequence acts as a weak TPOR agonist as a monomer and as a strong agonist when two monomers are cross-linked to form a homodimer. However, this peptide construct has some disadvantages for therapeutic use:

I) The peptide is conformationally highly flexible and therefore per se amenable to proteolytic degradation. This results in short plasma half lives. In addition, its susceptibility to proteolytic attack by protease in the stomach and intestine (pepsin, trypsin, elastase, chymotrypsin etc) as well as on the surface of the intestinal brush border membrane obviates its oral application for the treatment, e.g. of thrombocytopenia.

II) It is difficult to produce peptides such as those described in Cwirla et al. (1997) recombinantly. Small peptides are notoriously difficult to overexpress in high yield in microbial expression systems since they are often rapidly degraded by cellular proteases. Thus, chemical peptide synthesis is the method of choice, with all its known disadvantages such as the occurrence of unwanted side products (e.g. truncations due to pre-mature termination of the synthesis; or the incorporation of stereoisomeric amino acids).

Further TPO-antagonistic peptides have been reported in WO 03/031589. However, also these are charged with the above-mentioned shortcomings.

The above outlines are exemplary for the situation one is faced with when trying to establish dimeric or multimeric (poly)peptides as effector molecules with agonistic or antagonistic effects in the respective biological target system. It is thus evident that there is a need in the prior art for means and methods that allow the application of di- or multimeric peptide effector molecules which can be readily produced recombinantly and/or which have beneficial in vivo characteristics such as a long half life increased stability and bioavailability and the like.

Microproteins are described in the prior art as diverse small proteins, typically not longer than 50 residues in length, which share a common structural motif consisting of a cystine knot and a small triple-stranded β-sheet. These proteins are also known as the members of the inhibitor cystine knot (ICK) family (Le-Nguyen et al., 1990) of small proteins. They have a common architecture, but diverse biological activities and negligible amino acid sequence identity. Examples are (i) ω-conotoxin MVIIa, a 26-residue polypeptide found in the venom of the cone snail *Conus magus*, which acts as a neurotoxin by its high affinity binding to voltage-gated $Ca^{2+}$ channels (Kohno et al., 1995); (ii) potato carboxypeptidase inhibitor (PCI), a 39-amino acid peptide (Rees and Lipscomb, 1982); and (iii) EETI-II from the squirting cucumber *Ecballium elaterium* (Le-Nguyen et al., 1990).

All microproteins of the ICK family known so far have an inhibitory or antagonistic function which is based on the binding of a microprotein to the respective target molecule thereby blocking its activity. In addition, all microproteins known so far whether being open-chain or cyclic, exist as monomeric proteins.

As already mentioned above, there is a need in the prior art for a method that is particularly suited for producing agonistic or antagonistic peptide effector molecules. The prior art provides processes for the cyclisation or joining of peptide pieces that might in principle be useful for this purpose. However, these processes are generally disadvantageous because they require that the peptide starting material is provided by chemical synthesis, i.e. not recombinantly. Gaertner et al. (J. Biol. Chem. 269 (1994), 7224-7230) proposed a process for joining peptide pieces that can be applied to recombinantly produced peptides. But, it is not described to be applicable to microproteins. And, it has to be regarded unclear in light of the prior art knowledge whether it could be applicable to microproteins. The procedure described by Gaertner et al. requires the presence of a carboxyterminal hydrazide and it is not obvious based on the prior art how this can be generated when starting from recombinantly produced microproteins. Furthermore, the reaction scheme described by Gaertner et al. involves in a first step an oxidation reaction and after peptide joining a reduction. It is unknown so far whether these reaction conditions might result in unwanted reshuffling or opening of the three disulfide bonds that are present in a microprotein.

Summarizing the above, the technical problem underlying the present invention is the provision of a readily producible peptide structure that allows employing di- or multimeric peptides or polypeptides with improved in vivo characteristics such as increased half life, stability and/or bioavailability and the provision of corresponding methods for its production.

This technical problem is solved by the provision of the embodiments as characterized in the claims.

Accordingly, the present invention relates to a polypeptide comprising at least two microproteins.

With the polypeptides of the invention, a framework structure has been provided that allows to provide peptide functionalities in di- or multimeric form in a way that brings about improved functional properties, in particular improved in vivo characteristics, such as increased half life, improved stability and/or bioavailability compared to prior art di-/multimeric peptide structures. In addition, it is contemplated that polypeptides according to the present invention which are loaded with one or more effector peptides show an improved affinity and selectivity compared to prior art peptide di-/multimers due to an increased conformational fixation of the peptide and a concomitant reduction of conformational entropy. The polypeptide of the invention has furthermore the advantage to open up the possibility to introduce polyvalency or heterofunctionality by introducing more than one peptide by replacing more than one microprotein loop. A further advantageous feature of the polypeptides of the invention lies in the fact that protection from proteolytic cleavage at both termini can be easily achieved by using microproteins that are circular. These improved properties can be explained by the highly constrained topology the rigid microprotein three-dimensional structure imposes on the incorporated peptide sequences and by the advantageous properties that are intrinsic to microproteins.

Figure 3:
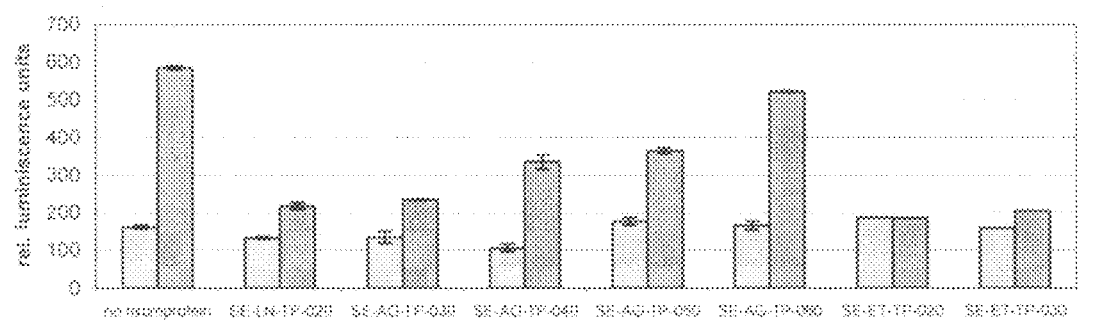

It could surprisingly be shown that functionalities that were known for peptide dimers described in the prior art, i.e. where the functional peptide moieties had a high degree of freedom as regards three-dimensional structure, could be observed for microprotein dimers into which the corresponding peptides had been-grafted. Using as a model the interaction of TPO-agonistic peptides with a hybrid TPO receptor, it could surprisingly be shown that such peptides, when grafted into dimeric microprotein scaffolds, could efficiently activate the TPO receptor (see appended Example 1). In particular, the unexpected finding was made that a TPOR binding sequence (IEGPTLRQWLAARA; SEQ ID NO: 7) can be transplanted into the scaffold of a microprotein without loss of affinity to the TPO-receptor and that, upon dimerization of the microprotein encompassing the receptor binding sequence, a fully active agonist is obtained that induces in a TPO-like manner the formation of megakaryocytes. As can be seen in FIG. 3, two microprotein scaffolds were used for the incorporation of the aforementioned peptide. One is based on the scaffold of the cystine-rich region derived from melanocortin receptor binding domain of human agouti related protein (Mc Nulty et al., 2001) AGRP (AGRP'), the other from the *Ecballium elaterium* trypsin inhibitor microprotein (Christmann et al., 1999). In AGRP' the binding loop that is responsible for binding to the melanocortin receptor (-CYCRFFNAFCYC-, SEQ ID NO.: 20, Joseph et al., 2003) was replaced by the TpoR binding sequence. Since no structural information of the peptide when bound to the receptor is available, different constructs were made aiming at forcing the introduced peptide into different loop conformations. This was achieved by introducing additional residues in the loop (SE-AG-TP-040 shown in Table 1 of Example 1) or by introducing two cysteine residues that may form a disulfide bond (SE-AG-TP-050 in Table 1 of Example 1). That a particular loop conformation is indeed required is shown in FIG. 3 since not all of the constructs displayed agonistic activity.

As a further advantage, the present invention allows to produce di- or multimeric peptide effector molecules at high yield recombinantly. In one embodiment, the polypeptides of the invention can be directly produced by applying recombinant expression if they are fusion proteins comprising at least two microproteins. In a further embodiment, the precursors, for instance the microprotein monomers, can be produced recombinantly and, afterwards, said precursors can be dimerized or multimerized by using prior art techniques or methods described hereunder. The recombinant expression of microproteins has for instance been described in EP 04 02 2455.2, Molina et al. (1992) or Schmoldt et al. (2004).

In connection with the present invention, the term "comprising at least two microproteins" means that at least two microproteins are so associated to one another that the association is not broken under conditions, where the polypeptide is used, e.g. under physiological conditions. In the present application, the polypeptide of the invention is also synonymously addressed as "microprotein di- or multimer". The term "multimer" is understood to mean three or more. The term "oligomer" or "oligomeric" in principle refers to the same meaning, but may, according to the context, also include dimers. The association of the at least two microproteins may be by covalent and/or non-covalent binding. Within the polypeptide of the invention, the microproteins may be present in every conceivable arrangement, depending on the intended application. In particular, the microproteins may be in a linear, circular or branched arrangement, or a mixture thereof. In linear structures, the microproteins may be connected either in a tandem arrangement, that is the C-terminus of one microprotein is linked to the N-terminus of another microprotein. Alternatively, the microproteins may be arranged head-to-head or tail-to-tail, that is the N-terminus of the one microprotein is linked to the N-terminus of another microprotein and/or the C-terminus of the one microprotein is linked to the C-terminus of another microprotein.

In a preferred embodiment, the polypeptide of the invention is cyclic.

The term "cyclic" is in accordance with any meaning a skilled reader would infer for cyclic peptide or polypeptide structures. In particular, the term "cyclic" may refer to one or more microprotein monomers contained in the polypeptide of the invention which is/are cyclic in itself/themselves, for instance forming a cystine knot with a circular peptide backbone conformation. Likewise, the term "cyclic" may refer to higher order cyclic structures within the polypeptide of the invention which involve more than one microprotein. A preferred example of such a higher order cyclic structure is a "macrocycle" in which the peptide backbones of at least two microproteins are connected to form a cycle. In this manner, the microproteins may be arranged either in tandem or head-to-head/tail-to-tail.

In a particularly preferred embodiment, the polypeptide of the invention forms a macrocycle, wherein the microproteins of said polypeptide are arranged so that the C-terminus of one microprotein is covalently bound to the N-terminus of another microprotein.

Within the polypeptide of the invention, the microproteins may be linked either directly or, what is preferred, via a linker molecule. Preferably, the linker molecule is a bifunctional or oligofunctional linker molecule. "Bifunctional" means that two microproteins can be covalently coupled by chemical or enzymatic means to one linker molecule. "Oligofunctional" means that more than two microproteins can be covalently coupled by chemical or enzymatic means to one linker molecule. Linker molecules suitable for connecting two or more peptide or polypeptide moieties are widely described in the prior art, such as in Baumert, Methods Enzymol. 172 (1989), 584-609; Yoshitake Eur. J. Biochem. 101 (1979), 395-399; Pierce Chemicals (1999), Double agents cross-linking reagents selection guide, Pierce Chemicals, Rockford, Ill., USA; Peters, Annu. Rev. Biochem. 46 (1977), 523-551; and Fasold, Angew. Chem. Int. Ed. Engl. 10 (1971), 795-801. Suitable Linker molecules are therefore known to a skilled person, in particular in regard to their provision as well as their application. Typically, linker molecules serve for instance the purpose of providing a space between two protein domains, in this case microproteins, and thereby allow e.g. correct folding of the domains into their functional three-dimensional structure. Furthermore, linker molecules may provide the distance between two domains that is necessary for the effective fitting of the two domains into their target structure, e.g. a dimeric protein receptor.

Preferably, direct linkage or linkage via a linker molecule is realized via peptide bonds. The linker molecule may in this case preferably be a peptide. According to this embodiment, it is possible to produce the microprotein di-/multimer recombinantly, i.e. as a fusion protein encoded by a corresponding expression construct. Peptide linkers are preferably relatively short, for instance consisting of not more than 10 amino acids, preferably of not more than 5 amino acids.

For certain applications, it may be required to break the association between two microproteins in a polypeptide of the invention. In this context, it is preferable that the microproteins are connected via a cleavable linker. To a person skilled in the art, corresponding cleavable linkers are familiar from the literature. For example, the cleavable linker may be a peptide linker, said peptide linker for instance comprising an enzymatic cleavage site, such as a thrombin cleavage site. In the alternative, the cleavable linker, preferably the peptide linker, may also be designed to be susceptible to cleavage mechanisms other than enzymatic ones, for instance to chemical or physical means.

Furthermore, the linker molecule connecting two microproteins within a polypeptide of the invention may be designed to be able to perform a certain movement, as is the case for linkers being a flexible hinge. Here, the skilled practitioner may refer to prior art literature describing corresponding peptidic or non-peptidic linker structures It is preferred that, in the polypeptide of the invention, the at least two microproteins are linked by non-peptidic coupling. Preferentially, said non-peptidic coupling comprises a bifunctional or oligofunctional linker molecule. Particularly preferred are linker molecules selected from adipinic acid hydrazide, bis-succinimidyl-suberate (DSS) and EDTA-hydrazide.

The term "microprotein" has a well-established meaning in the prior art literature and generally refers to polypeptides with a relatively small size of not more than 50 amino acids and a defined structure based on intra-molecular disulfide bonds. Microproteins are typically highly stable and resistant to heat, pH and proteolytic degradation. The current knowledge on microproteins, in particular in regard to their structure and occurrence, is for instance reviewed in Craik (2001); Pallaghy (1994); and Craik (J. Mol. Biol. 294 (1999), 1327-1336).

In a preferred embodiment, each of said microproteins in the polypeptide of the invention comprises at least six cysteine residues, of which six cysteine residues are connected via disulphide bonds so as to form a cystine knot.

Microproteins are also known as inhibitor cystine knot (ICK) polypeptides and are also called like that in the following explanations.

The term "cystine knot" refers to a three-dimensional structure formed by the ICK polypeptides which are characterized by a small triple β-sheet which is stabilized by a three-disulfide bond framework which comprises an embedded ring formed by two disulphide bonds and their connecting backbone segments, through which a third disulfide bond is threaded. Preferably, the cystine knot is formed by six conserved cysteine residues and the connecting backbone segments, wherein the first disulfide bond is between the first and the fourth cysteine residue, the second disulfide bond between the second and the fifth cysteine residue and the third disulfide bond between the third and the sixth cysteine residue, the third disulfide bond being threaded through the ring formed by the other two disulfide bonds and their connecting backbone segments. If considered suitable, a disulfide bond may be replaced by a chemical equivalent thereof which likewise ensures the formation of the overall topology of a cystine knot. For testing whether a given microprotein has formed the correct cystine knot, a skilled person can determine which cystine residues are connected with one another. This can, for instance, be done according to techniques described in Gorasson (J. Biol. Chem. 278 (2003), 48188-48196) and Horn (J. Biol. Chem. 279 (2004), 35867-35878). Microproteins with a cystine knot are for instance described in Craik (2001); Pallaghy (1994); and Craik (J. Mol. Biol. 294 (1999), 1327-1336).

The microproteins for use in connection with the present invention may have a peptide backbone with an open or a circular conformation. The open conformation preferably refers to microproteins with an amino-group at the N-terminus and a carboxyl-group at the C-terminus. However, any modifications of the termini, along with what a skilled person envisages based on the state of the art in peptide chemistry, is also contemplated. In the closed conformation, the ends of the peptide backbone of the microproteins are connected, preferably via a covalent bond, more preferably via an amide (i.e. peptide) bond. Microproteins with a closed conformation having a cystine knot topology are known in the prior art as "cyclotides" and their knot as "cyclic cystine knot (CCK)". Such cyclotides are for instance described in WO 01/27147 and Craik (Curr. Opinion in Drug Discovery & Development 5 (2002), 251-260).

It is furthermore preferred that the microproteins within the polypeptide of the present invention comprise the amino acid motif $CX_3$-$CX_4$-$CX_{4-7}$-$CX_1$-$CX_{4-5}$-$CX_{5-7}$ (SEQ ID NO: 8), with X meaning independently from each other any amino acid residue. C means, in accordance with the standard nomenclature, cysteine. Preferably, the amino acids X are not cysteine. It is furthermore preferred that the cysteine residues C in that sequence form a cystine knot as defined above.

In accordance with a further preferred embodiment of the invention, the microproteins have a length of between 28 and 40 amino acids.

For certain applications, it may be advantageous that one or more microproteins within the polypeptide of the invention do not exceed a certain maximum size. This may for example apply when a microprotein monomer has to fit into a pocket of the target protein, such as the catalytic site of an enzyme. Accordingly, it is particularly preferred that the microproteins for use in connection with the present invention have a length of up to 35 amino acids, more preferably of up to 32 amino acids, and most preferably of up to 30 amino acids. Preferably, the above-mentioned preferred size ranges apply to one, more preferably two and—if applicable—still more preferably to at least three microproteins within the polypeptide of the invention. Most preferably, all of the microproteins within the polypeptide of the invention show any one of the above-mentioned size limitations.

A microprotein contained in the polypeptide of the invention may either be a wild-type microprotein or a modified microprotein. Modification may be by deletion, addition, substitution or other modifications known to a person skilled in peptide chemistry, such as by post-translational modifications.

In a preferred embodiment, a microprotein is used for the polypeptide of the invention where a functional peptide sequence is grafted into the microprotein. The term "grafting" refers in connection with the present invention to the replacement of parts of the microprotein sequence by another peptide sequence which is intended to have a desired function. This function may be the binding of a target molecule such as a target protein, like, e.g. receptors, ligands, antibodies, antigens, enzymes or other binding proteins. The binding of the peptide sequence to the target molecule may have an inhibitory or activating effect on the target molecule. Advantageously, a part of the microprotein is selected for replacement which is not essential for the formation of the three-dimensional structure of the microprotein. Numerous approaches for preparing grafted microproteins have been described in the prior art for monomeric microproteins, see for instance Craik (Curr. Op. Drug Discovery Design 5 (2002), 251-260), WO 01/27147, Barry, Structure 12 (2004), 85-94; Craik, Toxicon 39 (2001), 1809-1813; Chiche, Current Protein and Peptide Science 5 (2004), 341-349; Rosengren, J. Biol. Chem. 278 (2003), 8606-8616; and Christmann, Protein Eng. 9 (1999), 797-806. These citations are herewith incorporated by reference. Typically, for the grafting, a loop of the microprotein is replaced or partially replaced by a desired amino acid sequence, wherein said loop does not comprise an element critical to the formation of the microprotein's three-dimensional structure. The grafting may be carried out according to methods described in the literature. Commonly, the incorporation of the desired amino acid sequence is done by accordingly mutagenizing the microprotein coding sequence, for instance by using customary in situ mutagenisation techniques, such as techniques involving PCR amplification. The grafted microprotein may then be provided upon expression of the mutagenized coding sequence in a suitable host. For this purpose, standard recombinant DNA manipulation and expression methods such as described in Sambrook et al. (2001) may be applied.

Alternatively, the grafted microprotein may also be produced by methods other than recombinant expression for instance by way of post-translational chemical manipulation of the microprotein. In a preferred way, the grafted microprotein is produced according to the method of the invention involving the formation of hydrazone bonds described further below.

The microproteins for use in connection with the present invention may consist solely of amino acids, preferably naturally occurring amino acids. However, encompassed are also microproteins which are derivatized in accordance with techniques familiar to one skilled in peptide and polypeptide chemistry. Such derivatives may for instance include the replacement of one or more amino acids with analogues such as chemically modified amino acids, the cyclisation at the N- and C-termini or conjugation with functional moieties that may for instance improve the therapeutical effect of the microproteins. The inclusion of derivatized moieties may, e.g., improve the stability, solubility, the biological half life or absorption of the polypeptide. The moieties may also reduce or eliminate any undesirable side effects of the microprotein. An overview for suitable moieties can be found, e.g., in Remington's Pharmaceutical Sciences by E. W. Martin ($18^{th}$ ed., Mack Publishing Co., Easton, Pa. (1990)). Polyethylene glycol (PEG) is an example for such a chemical moiety which may be used for the preparation of therapeutic proteins. The attachment of PEG to proteins has been shown to protect them against proteolysis (Sada et al., J. Fermentation Bioengineering 71 (1991), 137-139). Various methods are available for the attachment of certain PEG moieties to proteins (for review see: Abuchowski et al., in "Enzymes as Drugs"; Holcerberg and Roberts, eds. (1981), 367-383). Generally, PEG molecules are connected to the protein via a reactive group found on the protein. Amino groups, e.g. on lysines or the amino terminus of the protein are convenient for this attachment among others. Further chemical modifications which may be used for preparing therapeutically useful microproteins include the addition of cross-linking reagents such as glutaraldehyde, the addition of alcohols such as glycol or ethanol or the addition of sulhydroxide-blocking or modifying reagents such as phosphorylation, acetylation, oxidation, glucosylation, ribosylation of side chain residues, binding of heavy metal atoms and/or up to 10 N-terminal or C-terminal additional amino acid residues. Preferably, the latter residues are histidines or more preferably the residues RGS-$(His)_6$.

A further suitable derivatisation may be the fusion with one or more additional amino acid sequences. In such fusion proteins, the additional amino acid sequence may be linked to the microprotein sequence by covalent or non-covalent bonds, preferably peptide bonds. The linkage can be based on genetic fusion according to methods known in the art or can, for instance, be performed by chemical cross-linking as described in, e.g., WO 94/04686. The additional amino acid sequence may preferably be linked by a flexible linker, advantageously a polypeptide linker, wherein said polypeptide linker may comprise plural, hydrophilic, peptide-bonded amino acids of a length sufficient to span the distance between the C-terminal end of the tertiary structure formed by the additional sequence and the N-terminal end of the microprotein or vice versa. The fusion protein may comprise a cleavable linker or cleavage site for proteinases (e.g., CNBr cleavage or thrombin cleavage site; see FIG. 2).

Furthermore, said additional amino acid sequence typically has a predefined specificity or function, e.g., nuclear localization signals, transactivating domains, DNA-binding domains, hormone-binding domains, protein tags (GST, GFP, h-myc peptide, FLAG, HA peptide).

In a preferred embodiment, the microprotein is fused to barnase, preferably to inactive barnase. Preferably, barnase fusion is used in order to facilitate recombinant production of the microprotein and the barnase moiety is removed prior to integration of the microprotein into the polypeptide of the invention.

"Barnase" is an extracellular ribonuclease from *Bacillus amyloliquefaciens* (Fersht, 1993; Paddon, 1987). It has been shown previously (Schmoldt et al., 2004) that the fusion of a microprotein to barnase can bring about a number of advantages. In particular, when the microprotein is produced recombinantly by the expression in a host cell, such as *E. coli*, the fused barnase moiety has solubilizing effect. This may greatly reduce or completely avoid the need to isoate the expressed microprotein from inclusion bodies and to subsequently oxidize it to obtain the active disulphide-bonded conformation. Further advantages lie in the possibility to use barstar-barnase affinity for purifying the expressed microprotein from the crude extract (EP 04 02 2455,2) as well as in the feasibility to crystallize the fusion protein and to analyze the three-dimensional structure by using the known barnase structure as an input for a facilitated structure modeling (EP 04 02 2455,2).

If the barnase fusion is constructed using an active barnase, it may be necessary to co-express the barnase inhibitor barstar in sufficient amount since otherwise the barnase has a lethal effect on the host cell (Martsev, 2004). In view of this, it may be preferable to use an inactive mutant of barnase such as the one having His-102 replaced by Ala (see FIG. 2 and the corresponding figure legend). Thereby, the advantages connected with barnase fusions are maintained, while it is not necessary to additionally co-express barstar.

Microproteins for use in connection with the present invention may, e.g., be a naturally purified product, or a product of chemical synthetic procedures, or produced by recombinant techniques from a prokaryotic or eukaryotic host (for example, by bacterial, yeast, higher plant, insect and mammalian cells in culture).

For the provision of the microprotein via recombinant expression, an overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence.

It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of proteins. These promoters often lead to higher protein yields than do constitutive promoters. In order to obtain an optimum amount of protein, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

Transformation or transfection of suitable host cells can be carried out according to one of the methods mentioned above. The host cell is cultured in nutrient media meeting the requirements of the particular host cell used, in particular in respect of the pH value, temperature, salt concentration, aeration, antibiotics, vitamins, trace elements etc. The microprotein can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the protein. Finally, high performance liquid chromatography (HPLC) can be employed for final purification steps.

Depending upon the host employed in a recombinant production procedure, the expressed polypeptide may be glycosylated or may be non-glycosylated. The polypeptide may also include an initial methionine amino acid residue.

Preferably, the microprotein is first recombinantly produced as a fusion protein, advantageously with barnase, and then released from the fusion partner by cleavage at the fusion linkage and subsequent separation.

Likewise, the microprotein may be produced by any suitable standard peptide synthesis procedure as described in the art (see, e.g., Merrifield, Methods Enzymol. 289 (1997), 3-13; Hancock, Mol. Biotechnol. 4 (1995), 73-86; and Merrifield, Adv. Enzymol. Relat. Areas Mol. Biol. 32 (1969), 221-296), such as for instance that used in Example 1 (infra).

The polypeptide of the invention may be produced according to any suitable method familiar to a person skilled in the art and described in the literature. The above explanations concerning the design and production of microproteins may accordingly applied to the polypeptide of the invention, inasfar this is appropriate. It is to be noted that the polypeptide may comprise further structural elements, in addition to the microproteins and one or more optional linkers. This may refer to additional amino acid sequences that may be present N- or C-terminally and/or internally. Such amino acid sequences may for example be fusion partners that facilitate the expression and/or purification of the polypeptide or parts thereof, such as barnase, preferably inactivated barnase (see FIG. 2). The additional amino acid sequences may also serve other functions such as binding, stabilizing, detection and the like. A skilled person familiar with peptide and polypeptide engineering will know suitable amino acid sequences to take for the respective purpose. Furthermore, the polypeptide of the invention may comprise other structural elements, as for example resulting from glycosylation, phosphorylation, ribosylation, pegylation (attachment of PEG) or the loading with detectable or therapeutically effective moieties such as fluorophores, radionuclides and the like. Here again the skilled person familiar with peptide and polypeptide engineering will be aware of suitable means and methods.

In a particularly preferred embodiment, the polypeptide of the invention comprises at least two microproteins which comprise an amino acid sequence having a specific binding activity to a target protein.

The term "specific binding activity" means a high affinity compared to the affinity to proteins other than the target protein. Preferably, the affinity to the target protein is at least 100 times higher than to other proteins, more preferably at least 1000 times higher. Preferably, "specific" means that the amino acid sequence does not bind to a significant extent to proteins other than the specified target protein. Binding can be measured by classical methods, e.g. by equilibrium dialysis, where the target protein is placed together with the ligand in a dialysis bag and after equilibrium formation the distribution of the ligand is measured within and outside the dialysis bag. Alternatively, the target can be immobilized to a solid surface and binding of the ligand is measured in a concentration-dependent manner, e.g. by measuring the mass increase by surface plasmon resonance (BiaCore).

The term "target protein" may be any conceivable one or more proteins where the binding of the polypeptides of the invention may have a desirable effect In particular, the term "target protein" refers to proteins where the association of two or more of said proteins in a close proximity due to the binding of the polypeptide of the invention brings about a desirable effect. The proteins may in this case be homo- or heterodimers or -multimers, wherein homodi- or multimers are preferred, and even more preferred are homodimers. It is understood that, in a main aspect, the effect of the binding of the polypeptide of the invention to the target protein is based on the fact that at least two microproteins within the polypeptide of the invention each bind to one target protein so that at least two of the target proteins are brought into close proximity. It is furthermore understood that the local association of the target protein may either have an activating or an inhibiting effect on the target protein. For example, the local association of two subunits of a homodimeric receptor protein may lead to its activation, said activation for instance resulting in triggering a signal transduction cascade. On the other hand, the binding of the polypeptide of the invention to the substrate binding site of a multimeric enzyme may have an inhibitory effect on the enzyme. In a preferred embodiment, the binding of said polypeptide has substantially the same effect as a naturally occurring binding molecule (e.g. ligand) of the target protein. In this case, it is preferred that the polypeptide of the invention has at least 10%, more preferably at least 50%, still more preferably at least 100% and even more preferably at least 150% or 200% of the activity of the naturally occurring binding molecule (if calculated according to a standard method for determining the activity of said molecule).

In a particularly preferred embodiment of the polypeptide of the invention, the target protein is a membrane-bound receptor, advantageously a receptor which activates other proteins downstream of the signalling cascade when molecules of said receptor are brought into close proximity to each other.

The term "membrane-bound receptor" refers to receptor proteins which are located at the plasmamembrane of a cell, particularly as a transmembrane protein, and are able to bind a ligand. Preferably, the ligand is a peptide or a polypeptide. It is furthermore preferred that the receptor has a hetero- or homodimeric or -multimeric form, preferably a homodi- or multimeric, more preferably a homodimeric form, and wherein in said form the receptor has an activity that differs from the activity of the receptor when present in the monomeric form. This activity change is contemplated to be facilitated according to the present invention by binding of the polypeptide of the invention to the receptor. Advantageously, the receptor is active when present in the di- or multimeric form.

In the prior art literature, many membrane-bound receptors are described which correspond to the aforementioned definition and their activity may therefore be modulated by binding of the polypeptide of the invention thereto. Examples are EPO receptor, epidermal growth factor receptor, human growth hormone receptor, TGF-beta receptor, FGF receptor, members of the receptor tyrosine kinase family and at least some G-protein coupled receptors. Membrane-bound receptors are for example described in Schlessinger, Cell 110 (2002), 669-672; Spivak-Kroizman, J. Biol. Chem. 267 (1992), 8056-8063; Plotnikov, Cell 98 (1999), 641-650; Remy, Science 83 (1999), 990-993; and Angers, Annual Review of Pharmacology and Toxicology 42, (2002), 409-435.

A person skilled in the art is enabled to prepare polypeptides according to the invention that have the capacity to specifically bind to a given target protein, such as a membrane-bound receptor. Preferably, the structure of ligands that bind to the target protein is known and the relevant ligand structure can be grafted into the microprotein according to methods described in the prior art (see supra).

In the alternative, the microprotein itself has the desired binding activity. For instance, it has been found that there are microproteins that have a specific binding activity to the tetrameric enzyme tryptase (EP 04 02 2455.2). Thus, the di- or multimerisation of a wild-type microprotein or a variant thereof having the desired binding activity may also result in the provision of a polypeptide of the invention.

Furthermore, it is possible by applying state-of-the-art techniques to provide a peptide or polypeptide sequence having the intended binding activity to a given target protein, even when the structure of the cognate ligand is not yet elucidated. In this regard, it is herewith referred to suitable screening methods, three-dimensional structure determination and computer-aided modelling methods. The screening may be carried out according to custom methodologies using for instance phage-displayed peptide libraries as starting material. Furthermore, yeast two-hybrid screening or techniques derived therefrom may be applied. Once the peptide structure critical to target protein binding is determined, this peptide can be grafted into a suitable microprotein scaffold by corresponding methods described heretofore.

In a particularly preferred embodiment, the membrane-bound receptor is a thrombopoietin (TPO) receptor.

A polypeptide according to the invention that has a specific binding activity to a TPO receptor is contemplated to act as a TPO agonist. This is because a homodimerization of the TPO receptor is known to result in an induction of subsequent second messenger pathways. Such agonists may be useful for treating pathological conditions that require an increased platelet production, such conditions being for example thrombocytopenia.

Thus, according to this embodiment, the polypeptide of the invention is capable of stimulating a TPO receptor. The term "TPO receptor" refers to the naturally occurring TPO receptor (including all its functional allelic variants and isoforms), preferably the human TPO receptor, isolated or recombinantly produced, or to variants of the naturally occurring TPO receptor substantially having the same biological activity. This may for example refer to fusion constructs comprising an extracellular portion of the TPO receptor capable of binding TPO and a fusion partner capable of releasing a detectable cellular signal upon dimerization of the fusion construct by TPO binding. Such a variant TPO receptor is for example the hybrid TPO receptor used in the assays described in Example 1 (infra).

Figure 4:
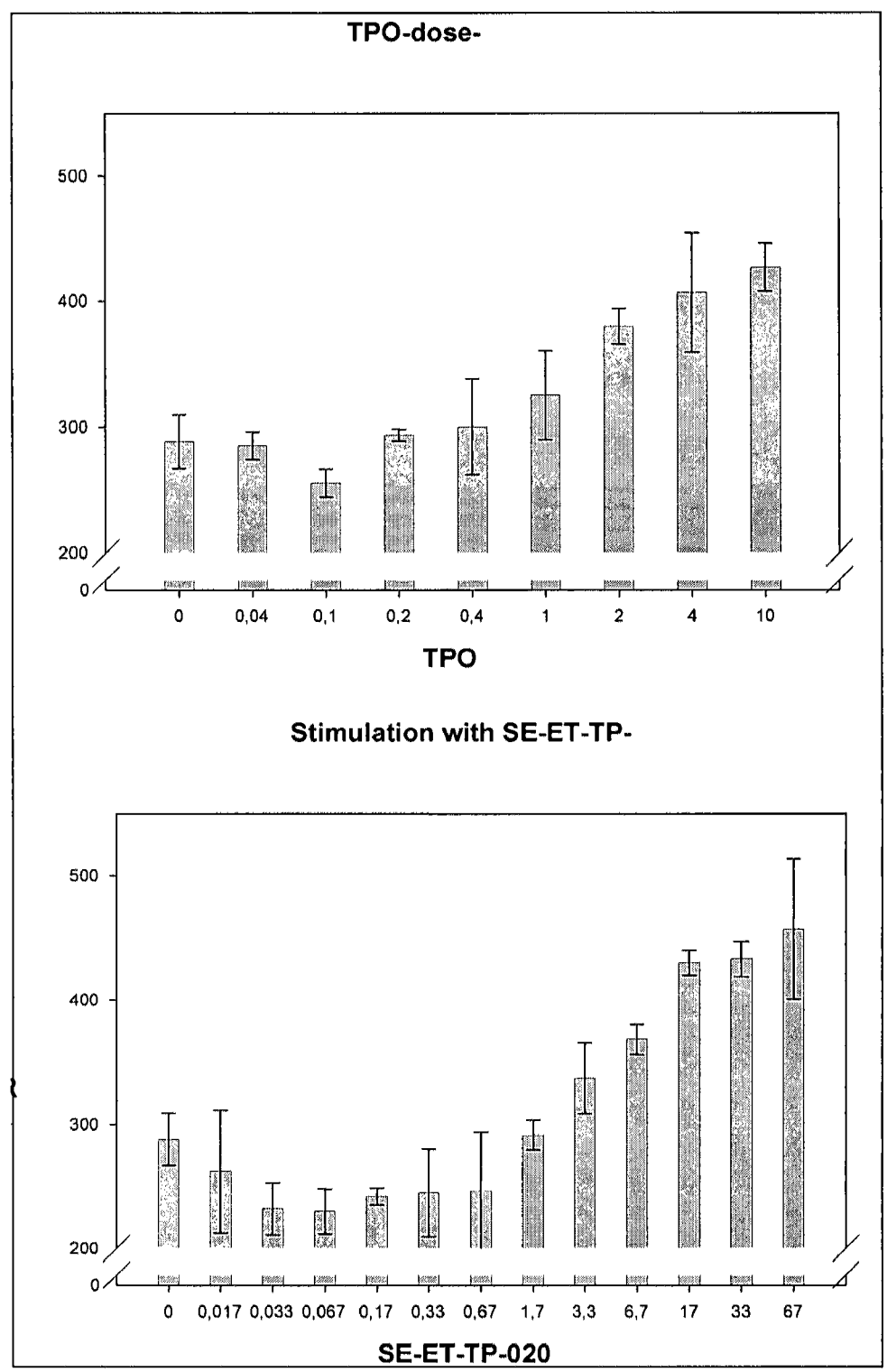
Figure 5:
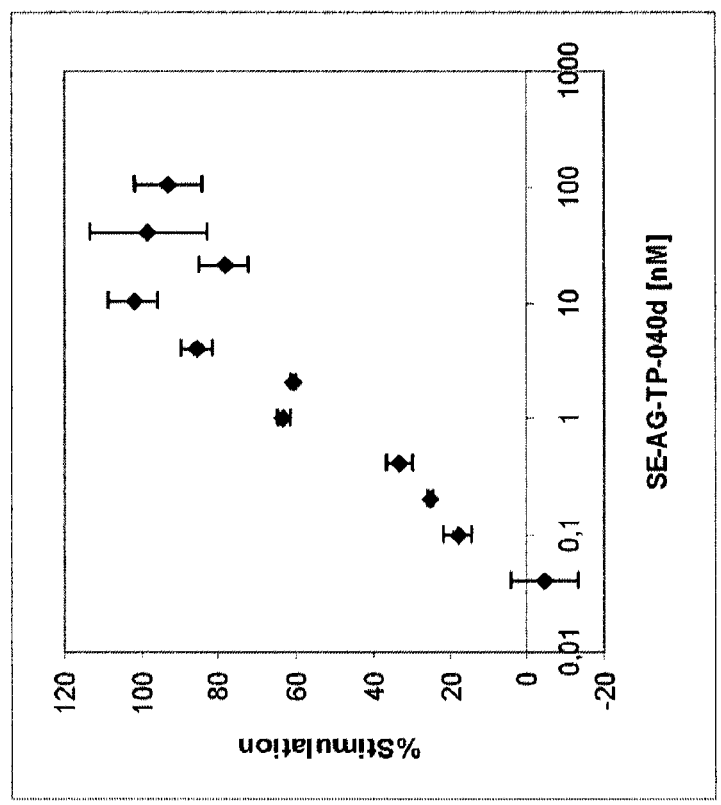
Figure 5:
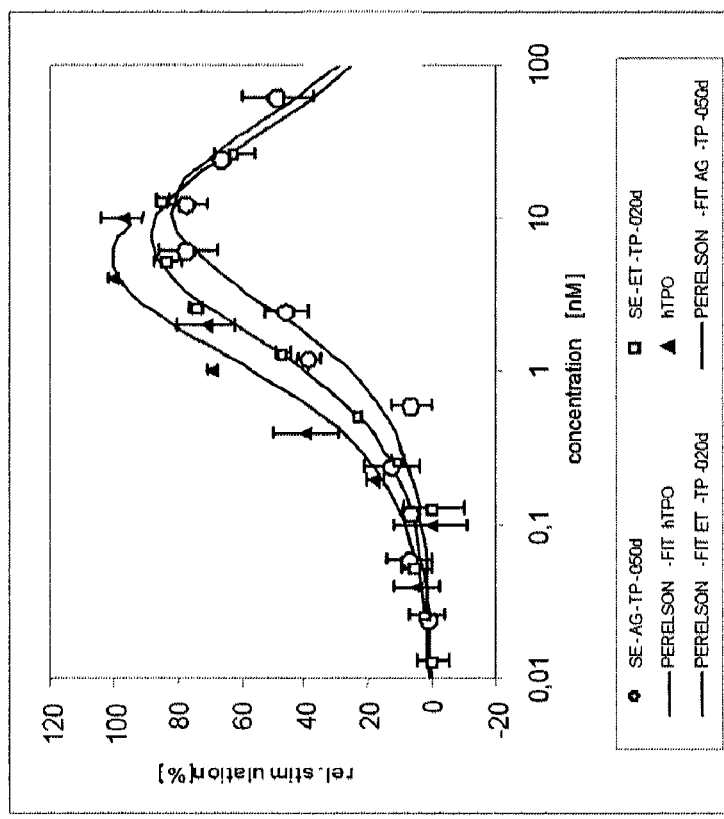
Figure 6:
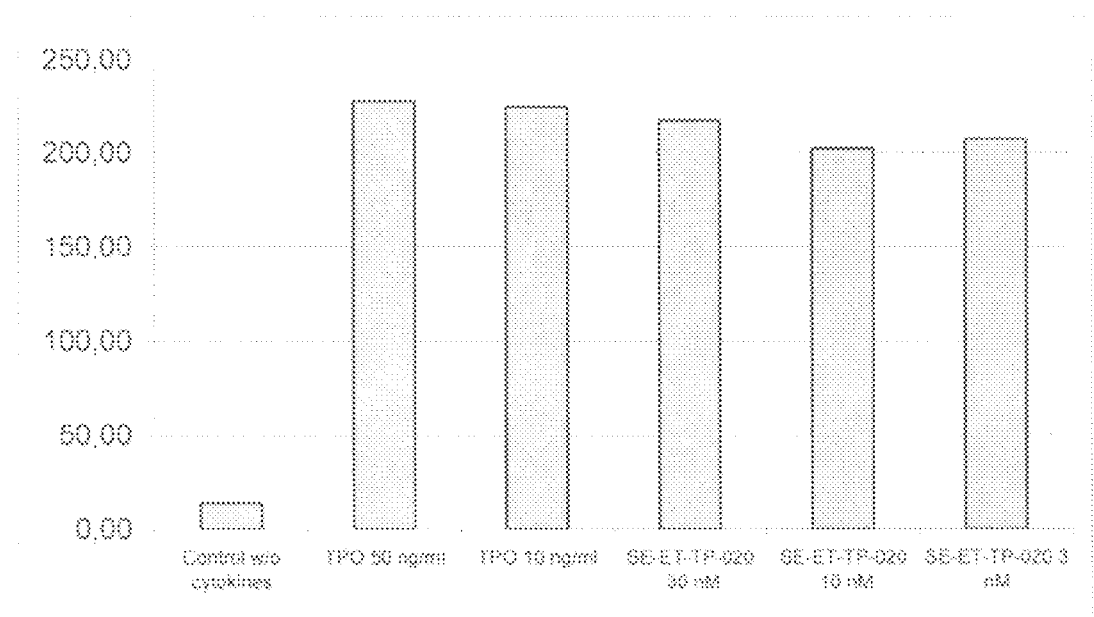
Figure 7:
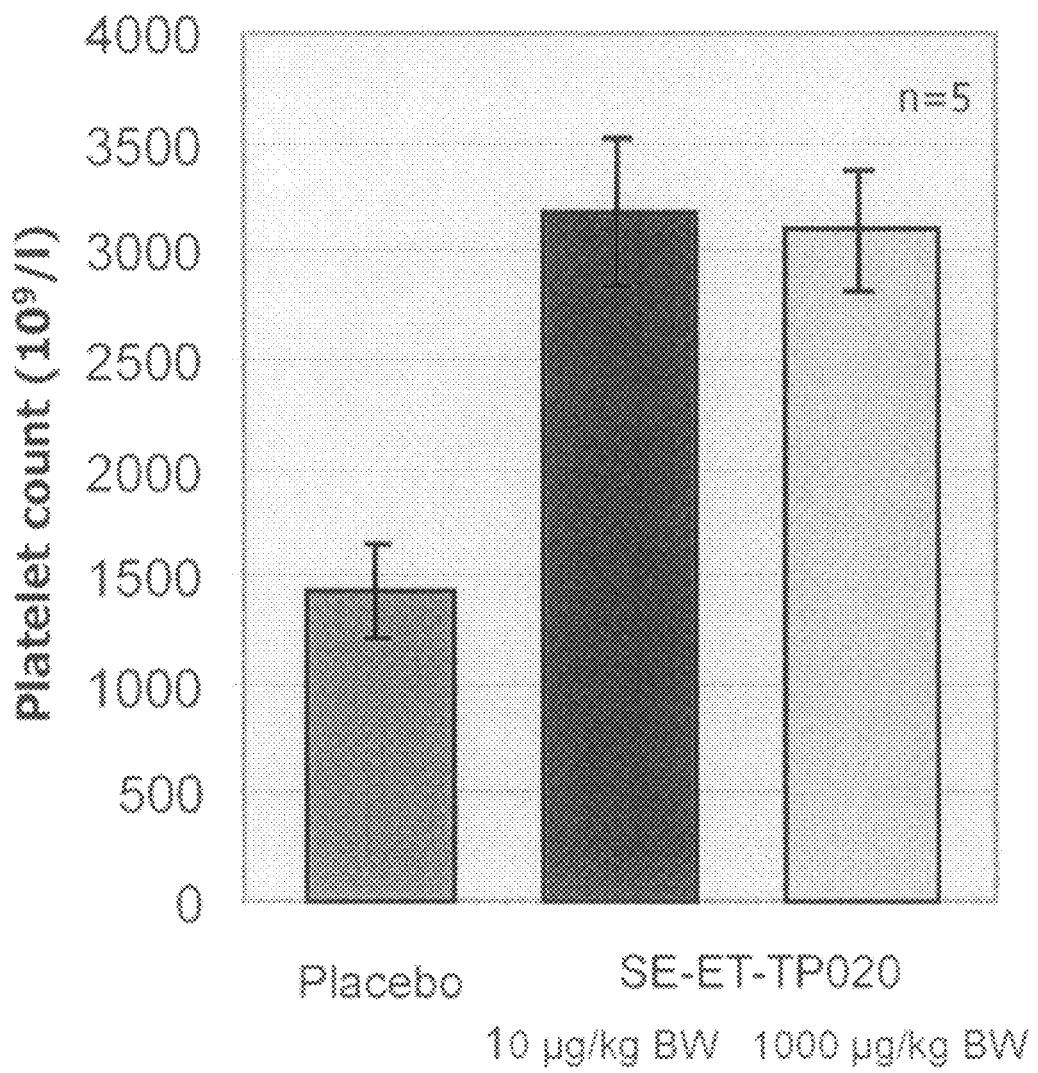

The term "capable of stimulating the TPO receptor" refers to the activity of a compound to bind to the TPO receptor, to induce dimerization of two TPO receptor molecules and thereby to trigger activation of the TPO receptor. This activity can be measured by methods known in the prior art such as described in Cwirla et al. (1997). Preferably, the activity is measured by using the TPO agonist assays described in Example 1 (infra), i.e. the luciferase assay the results of which are shown in FIGS. 4 and 5 or the marrow cell proliferation assay the results of which are shown in FIG. 6 or the in vivo platelet expansion test the results of which are shown in FIG. 7.

In a preferred form of the embodiment relating to TPO receptor-binding, the polypeptide of the invention comprises the amino acid sequence IEGPTLRQWLAARA (SEQ ID NO: 7). This amino acid sequence has been successfully used as a basis for producing TPO-agonistic microprotein dimers (see Example 1, infra).

Other peptides having the capacity to specifically bind the TPO receptor are described in the prior art such as in WO 03/031589. These peptide sequences may likewise be used in order to be grafted into the microprotein moieties contained in the polypeptide of the invention.

In a particularly preferred embodiment, the TPO receptor-binding polypeptide of the invention comprises at least two microproteins which comprise an amino acid sequence selected from the group consisting of:
(a) the amino acid sequence depicted in any one of SEQ ID NOs: 1 to 6
(b) a fragment of the amino acid sequence of (a), said fragment being capable of stimulating the TPO receptor when present in said polypeptide, and
(c) a functional equivalent in which at least one residue of the amino acid sequence or of the fragment of (a) or (b) is substituted, added and/or deleted, said functional equivalent being capable of stimulating the TPO receptor when present in said polypeptide.

Preferably at least two and, more preferably, all of the microproteins contained in the polypeptide of the invention have an amino acid sequence as defined in (a) to (c), supra. Furthermore preferred are dimers of microproteins having an amino acid sequence as defined in (a) to (c), supra, said dimerization advantageously being realized by using a bis-succinimidyl-suberate (DSS) linker. Dimers of microproteins as defined in (a), supra, are particularly preferred since they have been shown to be able to activate the TPO receptor (Example 1, infra).

According to this embodiment, also fragments of the microprotein sequences defined under (a), supra, may be used, provided said fragment is capable of stimulating the TPO receptor when present in the polypeptide of the invention. "When present in the polypeptide of the invention" is preferably intended to mean: "when present in the form of a dimer according to the above explanations". The term "fragment" has a clear meaning to a person skilled in the art and refers to a partial continuous sequence of amino acid residues within the amino acid sequence with reference to which the fragment is defined. Thus, compared to the reference amino acid sequence, the fragment lacks at least one amino acid residue at the N-terminus, at the C-terminus or at both termini. In the case of a circular reference sequence, the fragment lacks at least one amino acid residue at one position of said sequence, whereby the fragment may be circular or linear. Preferably, the fragment retains the six conserved cysteine residues and, by their presence, is capable of forming the cystine knot topology. It is furthermore preferred that the fragment retains the entire TPO receptor binding amino acid sequence contained in the corresponding sequence of (a).

The term "functional equivalent" refers to variants of a microprotein as defined in (a) or (b), in which at least one residue of the amino acid sequence or the fragment of (a) or (b) is substituted, added and/or deleted, said variant being capable of stimulating the TPO receptor when present in said polypeptide. Preferably, the functional equivalent has an amino acid sequence which comprises six cysteine residues which are connected via disulfide bonds so as to form a cystine knot.

A functional equivalent for use in the present invention may for example be a microprotein which is encoded by a polynucleotide the complementary strand of which hybridises with a nucleotide sequence encoding a microprotein as defined in (a) or (b), wherein said microprotein has the activity of stimulating the TPO receptor, when present in the polypeptide of the invention.

In this context, the term "hybridization" means hybridization under conventional hybridization conditions, preferably under stringent conditions, as for instance described in Sambrook and Russell (2001), Molecular Cloning: A Laboratory Manual, CSH Press, Cold Spring Harbor, N.Y., USA. In an especially preferred embodiment, the term "hybridization" means that hybridization occurs under the following conditions:

Hybridization buffer: 2×SSC; 10×Denhardt solution (Fikoll 400+PEG+BSA; ratio 1:1:1); 0.1% SDS; 5 mM EDTA; 50 mM $Na_2HPO_4$;
250 µg/ml of herring sperm DNA; 50 µg/ml of tRNA; or 0.25 M of sodium phosphate buffer, pH 7.2;
1 mM EDTA
7% SDS
Hybridization temperature T=60° C.
Washing buffer: 2×SSC; 0.1% SDS
Washing temperature T=60° C.

Polynucleotides encoding a functional equivalent which hybridize with a nucleotide sequence encoding a microprotein or fragment as defined in (a) or (b) can, in principle, be derived from any organism expressing such a protein or can encode modified versions thereof. Such hybridizing polynucleotides can for instance be isolated from genomic libraries or cDNA libraries of bacteria, fungi, plants or animals. Such hybridizing polynucleotides may be identified and isolated by using the polynucleotides encoding the microproteins described herein or parts or reverse complements thereof, for instance by hybridization according to standard methods (see for instance Sambrook and Russell (2001), Molecular Cloning: A Laboratory Manual, CSH Press, Cold Spring Harbor, N.Y., USA).

Such hybridizing polynucleotides also comprise fragments, derivatives and allelic variants of one of the polynucleotides encoding a microprotein as defined in (a) or (b), as long as the polynucleotide encodes a polypeptide being capable of stimulating the TPO receptor when present in the polypeptide of the invention. In this context, the term "derivative" means that the sequences of these polynucleotides differ from the sequence of one of the polynucleotides encoding a microprotein as defined supra in one or more positions and show a high degree of homology to these sequences, preferably within sequence ranges that are essential for protein function. Particularly preferred is that the derivative encodes an amino acid sequence comprising six cysteine residues which are connected via disulfide bonds so as to form a cystine knot.

The property of a polynucleotide to hybridize a nucleotide sequence may likewise mean that the polynucleotide encodes a polypeptide, which has a homology, that is to say a sequence identity, of at least 30%, preferably of at least 40%, more preferably of at least 50%, even more preferably of at least 60% and particularly preferred of at least 70%, especially preferred of at least 80% and even more preferred of at least 90% to the amino acid sequence of a microprotein as defined in (a) or (b), supra. Moreover, the property of a polynucleotide to hybridize a nucleotide sequence may mean that the polynucleotides has a homology, that is to say a sequence identity, of at least 40%, preferably of at least 50%, more preferably of at least 60%, even more preferably of more than 65%, in particular of at least 70%, especially preferred of at least 80%, in particular of at least 90% and even more preferred of at least 95% when compared to a nucleotide sequence encoding a microprotein as defined in (a) or (b), supra.

Preferably, the degree of homology is determined by comparing the respective sequence with the amino acid sequence of any one of SEQ ID NOs: 1 to 6. When the sequences which are compared do not have the same length, the degree of homology preferably refers to the percentage of amino acid residues or nucleotide residues in the shorter sequence which are identical to the respective residues in the longer sequence. The degree of homology can be determined conventionally using known computer programs such as the DNAstar program with the ClustalW analysis. This program can be obtained from DNASTAR, Inc., 1228 South Park Street, Madison, Wis. 53715 or from DNASTAR, Ltd., Abacus House, West Ealing, London W13 OAS UK (support@dnastar.com) and is accessible at the server of the EMBL outstation.

When using the Clustal analysis method to determine whether a particular sequence is, for instance, 80% identical to a reference sequence the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of homology of the hybridizing polynucleotide is calculated over the complete length of its coding sequence. It is furthermore preferred that such a hybridizing polynucleotide, and in particular the coding sequence comprised therein, has a length of at least 75 nucleotides and preferably at least 100 nucleotides.

Preferably, sequences hybridizing to a polynucleotide encoding a microprotein for use in connection with the invention comprise a region of homology of at least 90%, preferably of at least 93%, more preferably of at least 95%, still more preferably of at least 98% and particularly preferred of at least 99% identity to a polynucleotide encoding a specifically disclosed microprotein, wherein this region of homology has a length of at least 75 nucleotides and preferably of at least 100 nucleotides.

Homology, moreover, means that there is a functional and/or structural equivalence between the compared polynucleotides or the polypeptides encoded thereby. Polynucleotides which are homologous to the above-described molecules and represent derivatives of these molecules are normally variations of these molecules having the same biological function. They may be either naturally occurring variations, preferably orthologs of a polynucleotide encoding a microprotein as defined in (a) or (b), supra, for instance sequences from other alleles, varieties, species, etc., or may comprise mutations, wherein said mutations may have formed naturally or may have been produced by deliberate mutagenesis. The variants, for instance allelic variants, may be naturally occurring variants or variants produced by chemical synthesis or variants produced by recombinant DNA techniques or combinations thereof. Deviations from the polynucleotides encoding the above-described specific microproteins may have been produced, e.g., by deletion, substitution, insertion and/or recombination, e.g. by the fusion of portions of two or more different microproteins. Modification of nucleic acids, which can be effected to either DNA or RNA, can be carried out according to standard techniques known to the person skilled in the art (e.g. Sambrook and Russell, "Molecular Cloning, A Laboratory Manual"; CSH Press, Cold Spring Harbor, 2001 or Higgins and Hames (eds.) "Protein expression. A Practical Approach." Practical Approach Series No. 202. Oxford University Press, 1999). Preferably, amplification of DNA is accomplished by using polymerase chain reaction (PCR) and the modification is used by appropriate choice of primer oligonucleotides, containing e.g. mutations in respect to the template sequence (see, e.g. Landt, Gene 96 (1990), 125-128).

The polypeptides being variants of the concrete microproteins disclosed herein possess certain characteristics they have in common with said microproteins. These include for instance biological activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

In a further preferred embodiment, the present invention relates to polypeptides of the invention, wherein the target protein is a dimeric or oligomeric enzyme and wherein the at least microproteins of said polypeptide comprise an amino acid sequence which specifically binds to the active sites of said enzyme.

This embodiment refers in particular to enzymes which have a dimeric or multimeric structure and, correspondingly, two or a multitude of active sites. It is thus contemplated that a polypeptide of the invention can be directly designed so that binding peptides exposed by said polypeptide are able to fit into the active sites of the enzyme. The binding of the polypeptide to the enzyme is primarily conceived to have an inhibiting effect on the enzyme by blocking access of substrate to the active sites. Examples for di- or oligomeric enzymes include tryptase, proteasomes, cathepsin C or human granzyme A, only to note a few. Such enzymes are known from the prior art literature such as from Loidl, Biochemistry 96 (1999), 5418-5422; Turk, Biol. Chem. 378 (1997), 141-150; and Bell, Nat. Struct. Biol. 10 (2003), 527-534.

In an especially preferred embodiment, the dimeric or oligomeric enzyme is tryptase. Recently, it has been shown that microproteins may be used to inhibit tryptase (EP 04 02 2455.2). Since tryptase in its active form is a tetrameric enzyme with each monomer containing an active site, it is envisaged that dimers or multimers of microproteins are particularly suited as tryptase inhibitors.

The term "tryptase" includes the four closely related enzymes so far known which are α-, I-, II/β- and III-tryptase sharing a sequence identity between 90 and 98% (Miller, 1998; Vanderslice, 1990). Tryptase is the major secretory protease of human mast cells and is proposed to be involved in neuropeptide processing and tissue inflammation. Mature human tryptase is a tetrameric glycosylated molecule, is heparin-associated and composed of heterogenous, catalytically active subunits (see, e.g. Vanderslice et al., 1990; Miller et al., 1989, Sommerhoff et al., 1999). Tryptase is stored in mast cell secretory granules. After mast cell activation, human tryptase can be found in various biologic fluids. In connection with the present invention, the preferred target of the microproteins is mast cell tryptase, more preferably β-tryptase or α-tryptase. Preferably, the tryptase is human tryptase.

The activity of inhibiting tryptase can be tested by methods as described in the prior art and outlined in the following.

A suitable assay for tryptase inhibition activity is described in EP 04 02 2455.2. Accordingly, the concentration of inhibitory active inhibitor can be determined by titration with trypsin. For this purpose, bovine pancreatic trypsin may be standardized by active-site titration using p-Nitrophenyl p'-guanidinobenzoate (Chase & Shaw, 1970), the concentration of active inhibitor being calculated assuming a 1:1 interaction between the inhibitor and trypsin. Apparent equilibrium dissociation constants ($Ki_{app}$) for the complexes of the inhibitor with trypsin and tryptase can be determined essentially as described by Bieth (Bull. Eur. Physiopathol. Respir. 16 (Suppl.) (1980), 183-197). Briefly, increasing concentrations of an inhibitor are incubated with a constant concentration of an enzyme. Substrate is then added, and the residual enzyme activity measured. $Ki_{app}$-values are calculated by fitting the steady state velocities to the equation for tight binding inhibitors (Morrison, 1969) using non-linear regression analysis. The calculation of the apparent Ki-values (also designated $Ki_{app}$) which are indicative for the tryptase inhibiting activity of a given microprotein may be conducted according to Morrison (1969). Typically, polypeptides of the present preferred embodiment have a tryptase inhibiting activity with a Ki of not more than 1 mM, preferably not more than 0.5 mM, more preferably not more than 0.2 mM, still more preferably not more than 0.1 mM, further preferred not more than 0.05 mM, particularly preferred not more than 0.02 mM, especially preferred not more than 0.005 mM. Most preferred is a Ki of not more than 0.002 mM. It is understood that the values determined in the activity assays may vary within an error range typical for the particular assay system applied, preferably within a range of +/−20%, further preferred with +/−10% and particularly preferred within 5%.

It is further preferred that a polypeptide of the invention for use to inhibit tryptase additionally shows an inhibitory activity on trypsin. Since a test for trypsin inhibition may be indicative for the formation of the correct folding topology. A suitable trypsin inhibition assay is described in EP 04 02 2455.2 which is based on the methods described in Van Nostrand (1990) and Sinha (1991). Preferably, said polypeptide shows a Ki for trypsin in the range of not more than 1 nM and preferably of not more than 0.5 nM. Advantageously, in view of a high selectivity for tryptase which may be desirable for therapeutic applications, it is preferred that said polypeptide shows a comparatively low inhibitory activity with regard to other proteases, such as trypsin or blood co-aggulation factors.

The present invention furthermore relates to a nucleic acid molecule comprising a nucleotide sequence encoding the polypeptide of the invention according to the above-described embodiments.

This embodiment is intended to refer to nucleic acid molecules, wherein the comprised coding sequence reflects the dimeric or multimeric structure of the polypeptide of the invention. This means that, preferably, the nucleic acid molecule encodes a fusion protein in which the microprotein monomers are linked directly or via a peptide linker. However, it is also intended that the nucleic acid molecule encodes two or more microproteins as precursors for the polypeptide of the invention which only after appropriate processing steps, e.g. by chemical modification, give rise to the protein of the invention.

The nucleic acid molecules of the invention can be any type of polynucleotide, e.g. DNA molecules or RNA molecules or combinations thereof. These polynucleotides can be obtained by any suitable technique known in the art, they, for instance, may be produced synthetically or by recombinant techniques, in vivo or in vitro, such as PCR. Such polynucleotides may comprise any modification thereof that is known in the state of the art (see, e.g., U.S. Pat. No. 5,525,711, U.S. Pat. No. 4,711,955, U.S. Pat. No. 5,792,608 or EP 302175 for examples of modifications). Such polynucleotides may be single- or double-stranded, linear or circular, without any size limitation. Preferably, the nucleic acid molecules are DNA or mRNA.

The nucleic acid molecule encoding a fusion protein of the invention will generally be a recombinant nucleic molecule. The term "recombinant nucleic acid molecule" refers to any nucleic acid molecule that has been produced by a technique useful for artificially combining nucleic acid molecules or parts thereof that were beforehand not connected as in the resulting recombinant nucleic acid molecule. Suitable techniques are for example available from the prior art, as represented by Sambrook and Russell, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1989).

In a preferred embodiment, the nucleic acid molecule comprised in the recombinant nucleic acid molecule is operably linked to expression control sequences allowing expression in prokaryotic or eukaryotic cells. Suitable expression control sequences include promoters that are applicable in the target host organism. Such promoters are well known to the person skilled in the art for diverse hosts from the kingdoms of prokaryotic and eukaryotic organisms and are described in literature. For example, such promoters can be isolated from naturally occurring genes or can be synthetic or chimeric promoters. Likewise, the promoter can already be present in the target genome and may be linked to the coding sequence by a suitable technique known in the art, such as for example homologous recombination.

The nucleic acid molecule of the invention may be present in a vector, such as particularly plasmids, cosmids, viruses and bacteriophages used conventionally in genetic engineering. Such vectors are also part of the present invention.

In a preferred embodiment of the invention, the vectors of the invention are suitable for the transformation of fungal cells, plant cells, cells of microorganisms or animal cells, in particular mammalian cells. Preferably, such vectors are suitable for the transformation of microorganisms, such as yeast or bacteria, in particular of *E. coli*. Methods which are well known to those skilled in the art can be used to construct recombinant vectors; see, for example, the techniques described in Sambrook and Russell, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1989). Alternatively, the vectors may be liposomes into which the recombinant nucleic acid molecules of the invention can be reconstituted for delivery to target cells.

Advantageously, the nucleic acid molecules contained in the vectors and encoding a polypeptide of the invention are operably linked to one or more expression control elements permitting the expression of said polypeptide in a host cell.

The expression of the nucleic acid molecules of the invention in prokaryotic or eukaryotic cells, for instance in

*Escherichia coli*, may be interesting because it permits a more precise characterization of the biological activities of the proteins encoded by these molecules. In addition, it is possible to insert different additional mutations into the nucleic acid molecules by methods usual in molecular biology (see for instance Sambrook and Russell, 2001, Molecular Cloning, A Laboratory Manual, Cold Spring Harbor Laboratory Press, Cold Spring Harbor, N.Y.), leading to the synthesis of proteins possibly having modified biological properties. In this regard, it is on one hand possible to produce deletion mutants in which nucleic acid molecules are produced by progressive deletions from the 5' or 3' end of the coding DNA sequence, and said nucleic acid molecules lead to the synthesis of correspondingly shortened proteins. On the other hand, the introduction of point mutations is also conceivable at positions at which a modification of the amino acid sequence for instance influences the biological activity of the protein.

For genetic engineering in prokaryotic cells, the nucleic acid molecules of the invention or parts of these molecules can be introduced into plasmids which permit mutagenesis or sequence modification by recombination of DNA sequences. Standard methods (see Sambrook and Russell, 2001, Molecular Cloning: A laboratory manual, Cold Spring Harbor Laboratory Press, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

In a further aspect, the present invention relates to pharmaceutical compositions comprising the polypeptide of the invention or the nucleic acid molecule of the invention and, optionally, a pharmaceutically acceptable carrier.

Such pharmaceutical compositions comprise a therapeutically effective amount of the polypeptide or nucleic acid molecule and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin (see supra). Such compositions will contain a therapeutically effective amount of the aforementioned microprotein, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

In the context of the present invention the term "subject" means an individual in need of a therapy that can be related by administering the polypeptide of the invention to the individual. Preferably, the subject is a vertebrate, even more preferred a mammal, particularly preferred a human.

The term "administered" means administration of a therapeutically effective dose of the aforementioned pharmaceutical composition comprising the microprotein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intraarterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using methods known to those skilled in the art and dosages are optimized, e.g., in time, amount and/or composition. Progress can be monitored by periodic assessment. The pharmaceutical composition may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In a preferred embodiment, the pharmaceutical composition is formulated as an aerosol for inhalation.

In a further preferred embodiment, the pharmaceutical composition is formulated for the oral route of administration.

In another preferred embodiment, the pharmaceutical composition is formulated for transdermal administration.

In a preferred embodiment, the pharmaceutical composition of the invention is devised so that it can be administered to a patient in the form of a gene delivery vector which expresses the polypeptide of the invention. Furthermore preferred is that the cells are transformed with the vector ex vivo and the transformed cells are administered to the patient.

According to these embodiments, the pharmaceutical composition of the invention is a vector comprising and capable of expressing a polynucleotide encoding a polypeptide of the invention as described above. Such a vector can be an expression vector and/or a gene delivery vector. Expression vectors are in this context meant for use in ex vivo gene therapy techniques, i.e. suitable host cells are transfected outside the body and then administered to the subject. Gene delivery vectors are referred to herein as vectors suited for in vivo gene therapeutic applications, i.e. the vector is directly administered to the subject, either systemically or locally. The vector referred to herein may only consist of nucleic acid or may be complexed with additional compounds that enhance, for instance, transfer into the target cell, targeting, stability and/or bioavailability, e.g. in the circulatory system. Examples of such additional compounds are lipidic substances, polycations, membrane-disruptive peptides or other compounds, antibodies or fragments thereof or receptor-binding molecules specifically recognizing the target cell, etc. Expression or gene delivery vectors may preferably be derived from viruses such as retroviruses, vaccinia virus, adeno-associated virus, herpes viruses or bovine papilloma virus, and may be used for delivery into a targeted cell population, e.g. into cells of the respiratory tract. Methods which are well known to those skilled in the art can be used to construct recombinant expression or gene delivery vectors; see, for example, the techniques described in Sambrook and Russell, Molecular Cloning: A Laboratory Manual, Cold Spring Harbor Laboratory (2001) N.Y. and Ausubel, Current Protocols in Molecular Biology, Green Publishing Associates and Wiley Interscience, N.Y. (1989). Alternatively, the vectors can be reconstituted into liposomes for delivery to target cells. The vectors containing the a polynucleotide encoding the polypeptide of the invention can be transferred into a host cell by well-known methods, which vary depending on the type of cellular host. For example, calcium chloride transfection is commonly utilized for prokaryotic cells, whereas calcium phosphate treatment or electroporation may be used for other cellular hosts (see Sambrook, supra).

Suitable vectors and methods for ex-vivo or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO 94/29469; WO 97/00957 or Schaper, Current Opinion in Biotechnology 7 (1996), 635-640, and references cited therein. The vectors for use in this embodiment of the invention may be designed for direct introduction or for introduction via liposomes or viral vectors (e.g. adenoviral, retroviral) into the cell.

Preferred gene delivery vectors include baculovirus-, adenovirus- and vaccinia virus-based vectors. These are preferably non-replication competent.

The present invention also relates to the use of the polypeptide of the invention capable of binding and stimulating a TPO receptor as described above or the nucleic acid molecule of the invention encoding said polypeptide for the production of a pharmaceutical composition for treating or preventing a disease or condition which can be treated or prevented by stimulating the TPO receptor.

Accordingly, the invention likewise refers to a method for the treatment of an individual afflicted with a disease or condition that can be treated by stimulating the TPO receptor comprising administering to said individual an effective amount of a pharmaceutical composition comprising said polypeptide or said nucleic acid molecule and, optionally, a pharmaceutically acceptable carrier.

This medical application is based on the finding that microprotein dimers can be produced that effectively agonize the TPO receptor (Example 1, infra).

TPO plays a key role in the regulation of megakaryocytopoiesis, the process in which platelets are produced from bone marrow megakaryocytes (Kuter et al., 1994, Kaushansky et al., 1994; Wendling et al., 1994, Sauvage et al., 1994). TPO is produced in the liver but exerts its main function in the bone marrow, where it stimulates the differentiation of stem cells into megakaryocyte progenitors as well as megakaryocyte proliferation, polyploidization and, ultimately, their fragmentation into circulating platelet bodies. TPO is also the primary regulator of situations involving thrombocytopenia and has been shown in a number of studies to increase megakaryocytopoiesis in several ways: (1) it produces an increase of megakaryocyte size and number; (2) it produces an increase in DNA content in the form of polyploidy in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow. In view of these functions of TPO, a skilled practitioner will be readily aware of diseases that can be treated or prevented by stimulating the TPO receptor. Such diseases include diverse forms of thrombocytopenia, such as those specified below, hematologic diseases such as aplastic anemia, diverse forms of bone marrow failure, myelodysplastic syndrome and liver disease. TPO stimulation may also be of use in connection with transfusion, in particular in peripheral stem cell mobilization and harvest, platelet harvest (apharesis), in-vitro megakaryocyte or platelet production, or improved platelet storage, or with surgery, in particular major surgery (e.g. cardiac or general).

Platelets are necessary for blood clotting and when their numbers are very low a patient is at risk of death from catastrophic hemorrhage. Thus, the polypeptide of the invention being a TPO agonist has potential useful application in both the diagnosis and the treatment of various hematological disorders, for example, diseases primarily due to platelet defects. Likewise, such TPO agonists have potential application in the treatment of thrombocytopenic conditions, especially those derived from chemotherapy, radiation therapy, or bone marrow transplantation as treatment for cancer or lymphoma. Indeed, ongoing clinical trials in cancer patients have shown that recombinant human TPO is effective in decreasing the platelet nadir and enhancing platelet recovery when given with high-dose carboplatin chemotherapy (Basser et al., 1997). Similar results have also been obtained in clinical studies with pegylated megakaryocyte differentiation factor (peg-MGDF, a pegylated truncated N-terminal fragment of human TPO, Fanucchi et al., 1997). Because the slow recovery of platelet levels in patients suffering from thrombocytopenia is a serious problem, it is conceivable that the polypeptide of the invention can be successfully used for the treatment of thrombocytopenia by acting as a TPO mimetic.

In a preferred embodiment of the aforementioned second medical use or method of treatment, the disease or condition is selected from the group consisting of thrombocytopenia, aplastic anemia, bone marrow failure, myelodysplastic syndrome and liver disease.

The term "thrombocytopenia" has a clear meaning as recognized among experts in the field. The present preferred embodiment particularly refers to forms of thrombocytopenia which are e.g. induced by chemotherapy (hematologic malignancies or solid tumors), radiation therapy, bone marrow transplantation (allogenic or autologous) or peripheral stem cell transplantation. Furthermore, addressed are congenital thrombocytopenia, immune-mediated thrombocytopenia (immune thrombocytopenic purpura (ITP)), HIV-induced thrombocytopenia or drug-induced thrombocytopenia.

In accordance with the above, the invention also relates to the use of the polypeptide of the invention capable of binding and stimulating a TPO receptor as described above or the nucleic acid molecule of the invention encoding said polypeptide for stimulating the TPO receptor. Preferably, said use is in vitro.

In an additional aspect, the present invention relates to the use of the polypeptide of the invention capable of binding and inhibiting tryptase as described above or the nucleic acid molecule of the invention encoding said polypeptide for the production of a pharmaceutical composition for treating or preventing a disease or condition that can be treated or prevented by inhibiting the activity of tryptase.

Accordingly, the present invention likewise refers to a method for the treatment of an individual afflicted with a disease or condition that can be treated by inhibiting the activity of tryptase comprising administering to said individual an effective amount of a pharmaceutical composition comprising said polypeptide or said nucleic acid molecule and, optionally, a pharmaceutically acceptable carrier.

By the provision of this aspect of the invention, i.e. the use of tryptase-inhibiting polypeptides of the invention for therapeutic purposes, disadvantages are overcome that are known for low-molecular weight tryptase inhibitors (see, e.g., Newhouse, 2002). For instance, such small molecules may show a toxic effect to the organism to which they are applied due to a relatively low binding specificity causing binding to molecules other than tryptase. Compared to the small molecules, the microproteins within the polypeptide of the invention show a larger interaction surface so that a more selective binding can be expected for them. Furthermore, protein-based binding molecules typically have a lower dissociation rate constant than low-molecular weight molecules, thus, binding for a longer time to the target and therefore having more advantageous binding properties.

In addition, a further advantage over low-molecular weight tryptase inhibitors lies in the fact that the polypeptides of the invention can be expected not to be able to cross the membrane barrier. This prevents said polypeptides from binding to tryptase stored within mast cells which may potentially influence the physiological state of the mast cell negatively. Small molecules, by contrast, can often cross membranes. Moreover, especially cystine knot proteins are notoriously stable against enzymic or thermal degradation.

Due to the extensive prior art literature on using tryptase inhibitors for therapy (see, e.g. Newhouse (2002) and reference cited therein), a skilled practitioner will know what diseases can be treated or prevented by inhibiting the activity of tryptase.

Preferably said second medical use or method of treatment refers to a disease or condition selected from the group consisting of asthma, inflammation, psoriasis, pulmonary fibrosis, an interstitial lung disease, rheumatoid arthritis, gingivitis, peridontitis, an allergic reaction, allergic rhinitis, osteoarthritis, atherosclerosis, angiogenesis, multiple sclerosis and cancer.

In accordance with the above, the invention also relates to the use of the polypeptide of the invention capable of binding and inhibiting tryptase as described above or the nucleic acid molecule of the invention encoding said polypeptide for inhibiting the activity of tryptase. Preferably, said use is in vitro.

In a further aspect, the present invention also refers to a kit comprising the polypeptide of the invention or the nucleic acid molecule of the invention.

The components of the kit of the present invention may be packaged in containers such as vials, optionally in buffers and/or solutions. If appropriate, one or more of said components may be packaged in one and the same container. Additionally or alternatively, one or more of said components may be adsorbed to a solid support such as, e.g., a nitrocellulose filter or nylon membrane, or to the well of a microtitre-plate.

In a further aspect, the present invention relates to a method for forming a covalent bond in a microprotein comprising:
(a) providing a microprotein substrate comprising an N-terminal reactive carbonyl group and a C-terminal homoserine lactone residue; and
(b) reacting the microprotein substrate so as to convert said N-terminal group and said C-terminal residue into a hydrazone linkage.

This method is particularly useful for processing microproteins including the cyclisation of microproteins or the grafting of peptide sequences into a microprotein. Moreover, the method is of special utility for producing the dimers or multimers of multimers of the present invention.

The provision of this method represents an important facilitation of microproteins handling compared to prior art techniques for introducing a covalent bond in a microprotein. Current methods of for instance microprotein cyclization are based on chemical synthesis to introduce a C-terminal thioester (see Davies, 2003). These synthesis strategies are often problematic to optimize towards high yields and require in vitro disulfide bond formation which is often problematic to achieve since in substantial amounts side reaction products with wrong disulfides are found (Price-Carter et al., 1996). Intein-mediated cyclization is also problematic in this respect since the intein-microprotein fusion protein resides in the bacterial cytoplasm, where reducing conditions prevail that obviate disulfide bond formation.

Although it is still unknown how backbone cyclization occurs naturally, several techniques have been evolved to generate synthetic circular proteins (Evans et al., 1999, Scott et al., 1999 Tam and Lu, 1998). In general, there are two major strategies to achieve linkage of N- and C-termini: the first approach makes use of modified protein splicing elements called inteins which cleave peptide bonds at their C- and N-termini, respectively (Evans et al., 1999; Williams et al., 2002). If cloned in-frame to the N- and C-termini of a target protein an N-terminal cysteine and a C-terminal thioester is generated on it which leads spontaneously to the formation of a peptide bond connecting N- and C-terminus.

The second strategy relies on solid phase synthesis of the target protein with a N-terminal cysteine residue and a C-terminal α-thioester. If both termini are in close proximity to each order, a spontaneous reaction occurs resulting first in a thioester-linked intermediate, which undergoes intramolecular rearrangements to end up with a native peptide bond (Tam and Lu, 1998, Muir 2003). This strategy relies on a solid phase synthesis of the target protein followed by cyclization-oxidation or, vice versa, oxidation-cyclization. In the first approach, the linear Boc-synthesized and fully deprotected peptide is first "zipped" into a macrocycle, and then oxidized (Tam and Lu, 1998). Another method is to create from a fully deprotected peptide a folded open-chain precursor to get a suitable conformation for a head-to tail cyclization. Both methods have requirements and limitations. In particular, these methods require the chemical introduction of additional functions into the microproteins so that the methods are limited to the use of chemically synthesized microproteins. Thus, they do not work with recombinantly produced microproteins since these only contain natural amino acids. However, recombinant production is generally advantageous in view of costs and in view of the avoidance of undesired side products. The latter usually occurs with chemical microprotein synthesis due to synthesis errors leading to truncations and due to the formation of stereoisomers (racemates). The method of the present invention circumvents these restrictions and makes it possible to cyclize postsynthetically a recombinantly synthesized microprotein that is produced in an appropriate expression host with correct disulfide bond connectivities.

The recombinant production of the microproteins may be carried out according to any suitable method described in the prior art, and preferably as described herein. Preferred expression hosts of the present invention are *Escherichia coli* and *Pichia pastoris*.

The method of the present invention is based on the formation of a hydrazone bond between an N- and a C-terminus within a microprotein substrate. The term "microprotein substrate" refers to peptides or polypeptides which, based on their primary, secondary and/or tertiary structure, can be recognized as a microprotein, as a multitude of microproteins, or as a part thereof. Preferably, this term refers to precursors which, upon closing of the covalent bond, become a microprotein.

The provision of the N-terminal reactive carbonyl group and of the C-terminal homoserine lactone residue can be made according to suitable methods known in the art. In line with the present invention, the reactive carbonyl group must be such that it is capable of forming a hydrazone linkage with a C-terminal homoserine lactone residue. Preferably, the N-terminal reactive carbonyl group is a glyoxylyl group or a keto group. The keto group may be formed by suitable metal-catalyzed transamination of the N-terminal amino acid residue as is for example described in Dixon (Methods Enzymol. 25 (1972), 409-419).

In a preferred embodiment, the glyoxyl group is formed by mild oxidation of an N-terminal serine, threonine or hydroxylysine residue present in the microprotein substrate used.

In a preferred embodiment, the N-terminal serine or threonine residue of the microprotein substrate is provided by cleaving a precursor polypeptide comprising said microprotein substrate at the peptide bond between a methionine and a subsequent serine or threonine residue using cyanogen bromide.

Figure 8:
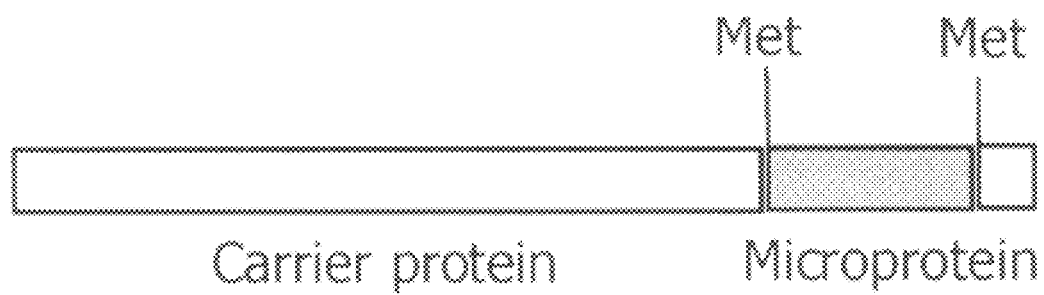

It is furthermore preferred that the C-terminal homoserine lactone residue of said microprotein substrate is provided by cleaving the peptide bond between a methionine and a subsequent amino acid residue using cyanogen bromide. Since according to this and the aforementioned preferred embodiments, cyanogen bromide is used as cleaving agent, both cleavage reactions can be performed simultaneously. It is therefore possible, and particularly preferred, that these steps are performed together, for instance using one carrier protein comprising the respective microprotein as the starting material. This situation is illustrated in FIG. 8.

The hydrazone formation of step (b) may be carried out according to any suitable method known in the art.

In a preferred embodiment, said step (b) comprises:
(i) reacting the C-terminal homoserine lactone residue to homoserine hydrazide;
(ii) reacting the homoserine hydrazide and the N-terminal reactive carbonyl group to generate a hydrazone; and
(iii) optionally reducing the hydrazone.

Figure 9:
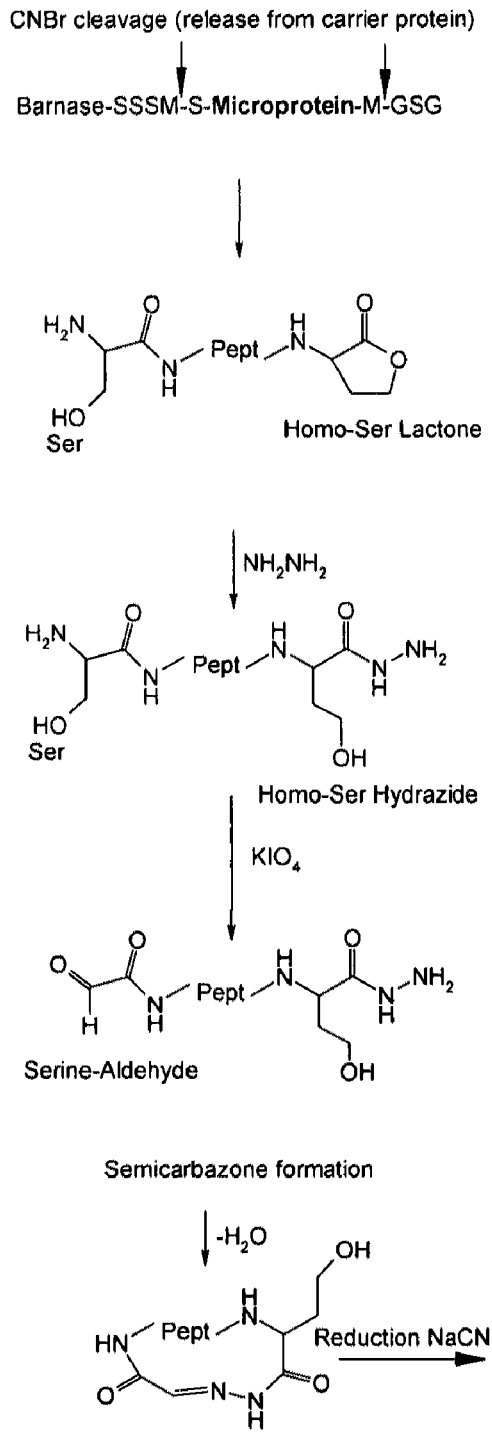
Figure 10:
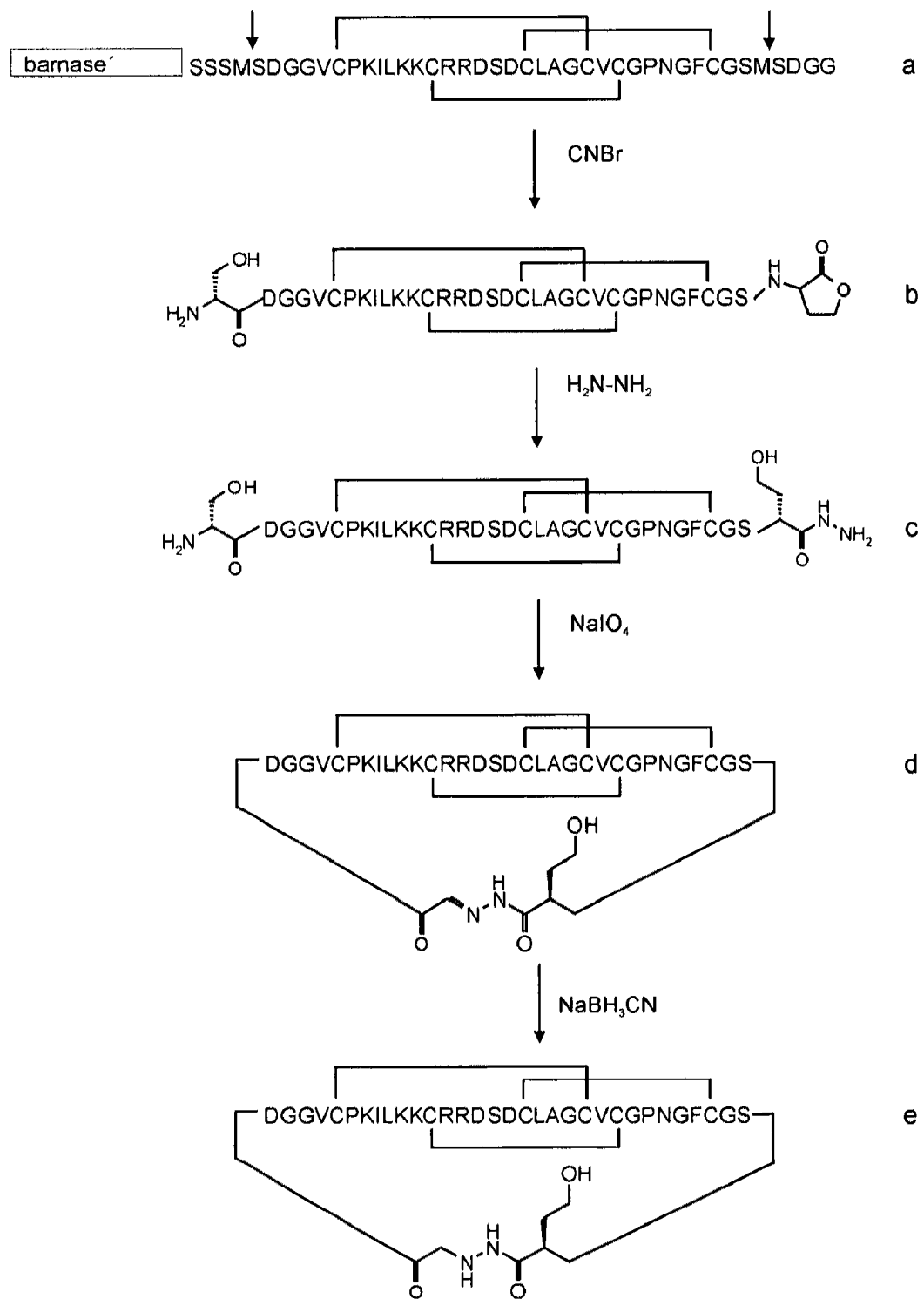

These method steps are illustrated for the example of a microprotein cyclization in FIGS. 9 and 10.

The microprotein can be released from the carrier protein by chemical cleavage using cyanogen bromide (CNBr) (FIG. 10a). CNBr cleaves the peptide bond of a protein at the C-terminus of methionine. By this reaction, the methionine residue is converted into a homoserine lactone. Upon cyanogen bromide cleavage of the fusion protein the carrier protein is released and a microprotein with an aminoterminal serine is released which contains a homoserine lactone at its carboxy-terminus (FIG. 10b), which is known to readily react with amines (Majerle et al., 2000). A major aspect of this invention relates to the reaction of this lactone with hydrazine to give a C-terminal hydrazide (FIG. 10c). Other methods of hydrazide formation either rely on chemical synthesis of activated esters or limited proteolytic cleavage in the presence of hydrazine (Gaertner et al., 1992, Rose et al., 1996). According to the present invention, hydrazide formation can preferably be easily accomplished by cyanogen bromide cleavage followed by hydrazinolysis. The aminoterminal serine can selectively be activated by oxidation using sodium periodate as described by Geoghegan and Stroh (1992). As a consequence, a glyoxylyl group is formed which readily reacts with the C-terminal hydrazide to form a hydrazone (FIG. 10d). The hydrazone can be reduced by sodium cyano borohydride to give a stable cyclic microprotein molecule (FIG. 10e). It is understood that, instead of the N-terminal serine, for example a threonine residue can also be used following essentially the same steps and reaction conditions.

In accordance with the above, it is a preferred embodiment of the method of the invention that the microprotein substrate is one single microprotein and the covalent bond formation is for cyclisation of the peptide backbone of said microprotein.

Figure 11:
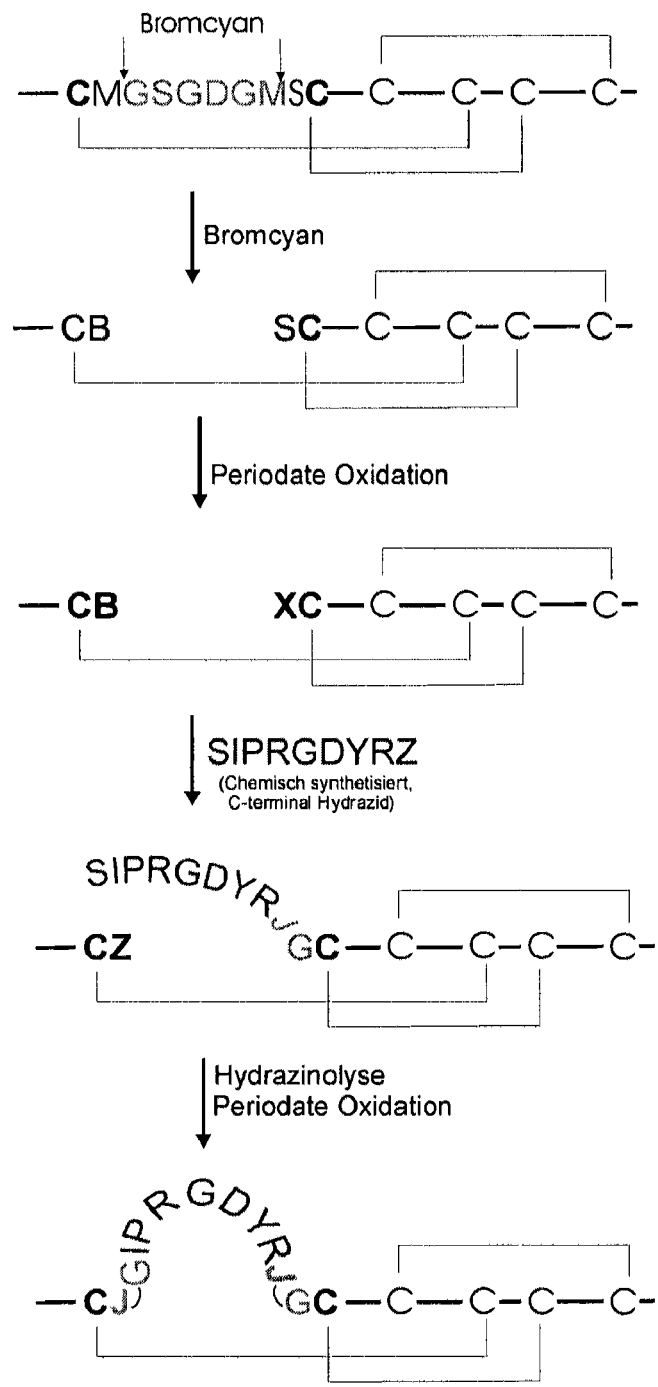

In an alternative preferred embodiment, the microprotein substrate is one single microprotein and the covalent bond formation is for ligating a graft peptide into the microprotein. This application is illustrated in FIG. 11.

Accordingly, in a particularly preferred embodiment, the method comprises the steps:

(A) cleaving a loop amino acid sequence of the microprotein to be replaced by the graft peptide at suitable peptide bonds between a methionine and a subsequent amino acid residue by using cyanogen bromide, wherein the subsequent amino acid residue at the C-terminus of said loop amino acid sequence is a serine or threonine residue;

(B) reacting the serine or threonine residue by mild oxidation so as to form a glyoxylyl group;

(C) reacting a graft peptide sequence comprising an N-terminal reactive carbonyl group and a C-terminal homoserine lactone hydrazide with the glyoxylyl group of the microprotein to generate a hydrazone;

(D) reacting the C-terminal homoserine lactone residue which resulted from the cleavage of step (A) to homoserine hydrazide; and (E) reacting the homoserine hydrazide of (D) with the N-terminal reactive carbonyl group of the graft peptide to generate a hydrazone.

The N-terminal reactive carbonyl group of the graft peptide preferably is a glyoxylyl group or a keto group, whereby the glyoxyl group is preferably formed by mild oxidation of an N-terminal serine, threonine or hydroxylysine residue.

In a further preferred embodiment of the method of the invention, the microprotein substrate comprises at least 2 microproteins and the covalent bond formation is for generating a dimer or an oligomer of said microproteins.

It is likewise preferred that the microprotein substrate comprises at least two microproteins and the covalent bond formation is for generating a macrocyclic dimeric or oligomeric microprotein.

These embodiments are especially suited for producing the polypeptides of the invention characterized above. In particular, the method comprising C-terminal activation via cyanogen bromide cleavage followed by hydrazinolysis and hydrazone formation with an aminoterminal aldehyde can also be applied to formation of homo- or heterodimeric microproteins. To this end, a microprotein may for example be recombinantly produced that contains a serine or thrionine residue at its aminoterminus and a methionine residue at its carboxy-terminus. Upon cyanogen bromide cleavage, an activated homoserine lactone is formed. The microprotein preparation can then be split into two equal parts. To one half, hydrazine hydrate is added which results in the formation of a carboxy-terminal homoserine lactone. The other half is aminoterminally oxidized by sodium periodate to give an aminoterminal glyoxal moiety. Both preparations are combined. Upon hydrazone formation a linear dimer is formed that can be reduced by sodium cyanoborohydride. The procedure of homoserine lactone hydrazinolysis and serine oxidation can be repeated. This results in glyoxal formation at the aminoterminus and hydrazide formation at the carboxyterminus of the dimer. Intramolecular hydrazone formation results in the formation of a macrocycle.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

The present invention is further described by reference to the following non-limiting figures and examples.

THE FIGURES SHOW

FIG. 1: gives examples for linked cyclic di- or multimeric microproteins according to the present invention.
  (A) C-N linked dimeric microprotein;
  (B) dimeric microprotein macrocycle; and
  (C) crosslinked microprotein oligomer.

Figure 2:
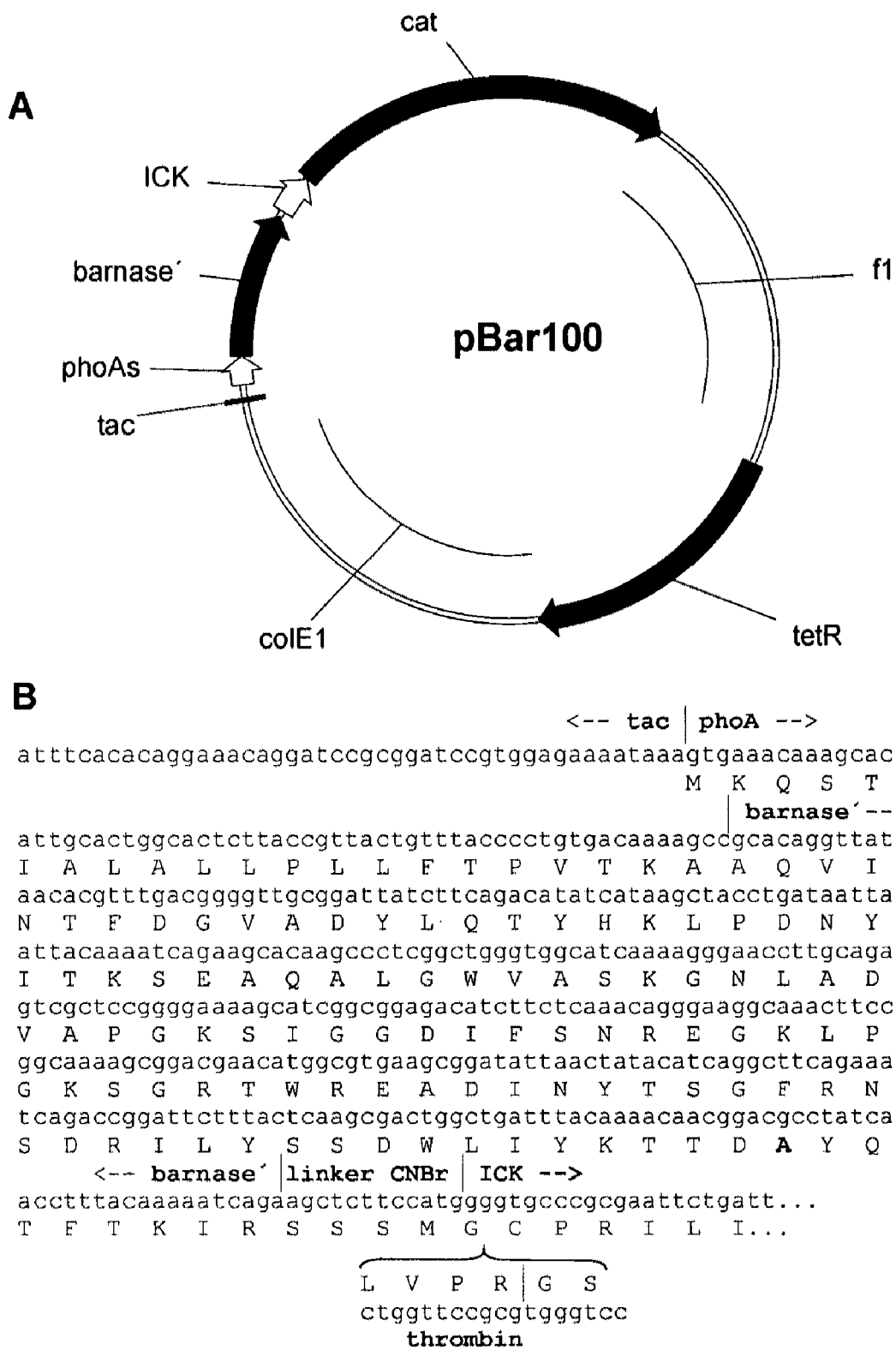

FIG. 2: illustrates the barnase'-ICK peptide fusion construct design. (A) Schematic representation of the plasmid pBar100 harboring the barnase' gene that leads to the expression of the enzymatically inactive H102A variant; f1, replication origin; cat, chloramphenicol resistance marker; tetR, tetracycline repressor encoding gene; colE1, colE1 replication origin; tac, tac promotor sequence; phoAs, alkaline phosphatase periplasmic signal sequence; ICK, ICK peptide encoding sequence. (B) DNA and protein sequence of the barnase'-ICK peptide fusion. The exchanged amino acid at position #102 of barnase (H102A) is indicated in bold letters. In the pBar100 series of expression vectors, a single methionine codon resides at the junction of barnase' and ICK peptide coding sequence that can be used for chemical cleavage of the fusion protein with cyanogen bromide. The pBar100Throm vector encodes in addition a thrombin recognition site (LVPRGS; SEQ ID NO: 9).

FIG. 3: shows the effects of various microproteins on TPO-mediated receptor activation. The assay detects dimerization of TPOR extracellular domains in a luciferase reporter gene assay. Grey: measurement of luminescence after addition of 500 nM of the respective microprotein. Green: luminescence when recombinant human TPO (5 nM) is added together with the respective compound.

FIG. 4: shows the dose-dependend activation of a hybrid TPO receptor by the addition of dimeric SE-ET-TP-020 (B) in comparison with the activation effected by recombinant human TPO (A).

FIG. 5: shows the dose-dependent activation of a hybrid TPO receptor by the addition of dimeric SE-AG-TP-050 and dimeric SE-AG-TP-020 (FIG. 5A) and dimeric SE-AG-TP-040 (FIG. 5B).

FIG. 6: demonstrates the induction of marrow cell proliferation by the addition of recombinant human TPO or dimeric SE-ET-TP-020. The number of colonies of large cells is given.

FIG. 7: shows that Balb/c mice treated with dimeric SE-ET-TP-020 produced an approximately two-fold increased platelet titer compared to control mice that underwent placebo treatment.

FIG. 8: is a schematic drawing of a fusion protein comprising a carrier protein and a microprotein that is flanked at both ends by a methionine residue.

FIG. 9: provides a schematic outline of the cyclization of a microprotein by cyanogen bromide cleavage carboxyterminal to the flanking methionines followed by hydrazide formation, aminoterminal serine oxidation, intramolecular cyclization and reduction of the resulting hydrazone.

FIG. 10: shows schematically the cyclization of a microprotein by cyanogen bromide cleavage carboxyterminal to the flanking methionines followed by hydrazide formation, aminoterminal serine oxidation, intramolecular cyclization and reduction of the hydrazone bond.

FIG. 11: presents the replacement of a microprotein loop by chemical ligation based on hydrazone formation.

Z: homoserine lactone hydrazide; B: homoserine lactone; X: serine aldehyde; and J: homoserine. Note that the incorporated peptide was chemically synthesized and has a C-terminal hydrazide (Z).

Figure 12:
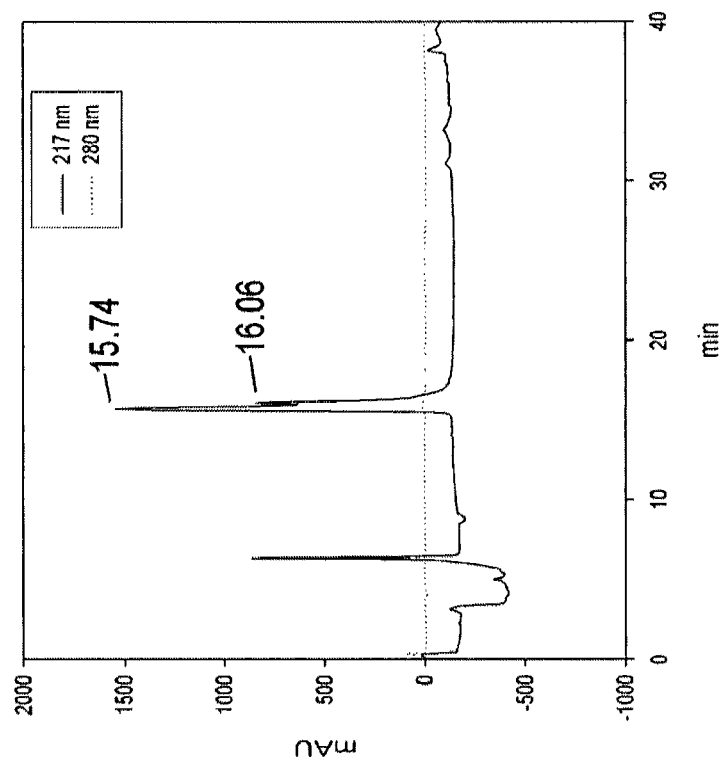
Figure 12:
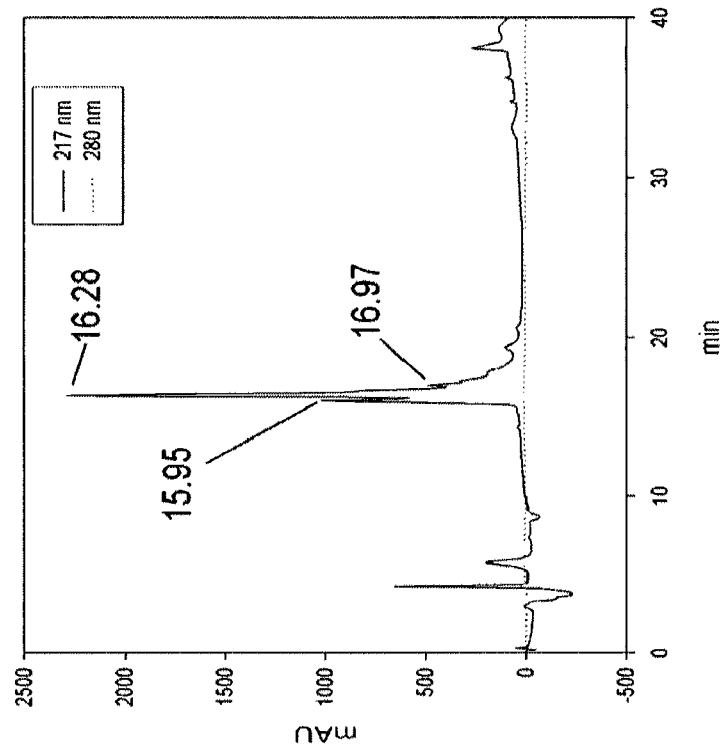

FIG. 12: depicts a RP-HPLC analysis of the conversion of cyclo-McoEeTI homoserine lactone (A) to cyclo-McoEeTI hydrazide (B). The respective time of elution from the RP column is given in the chromatogram.

Figure 13:
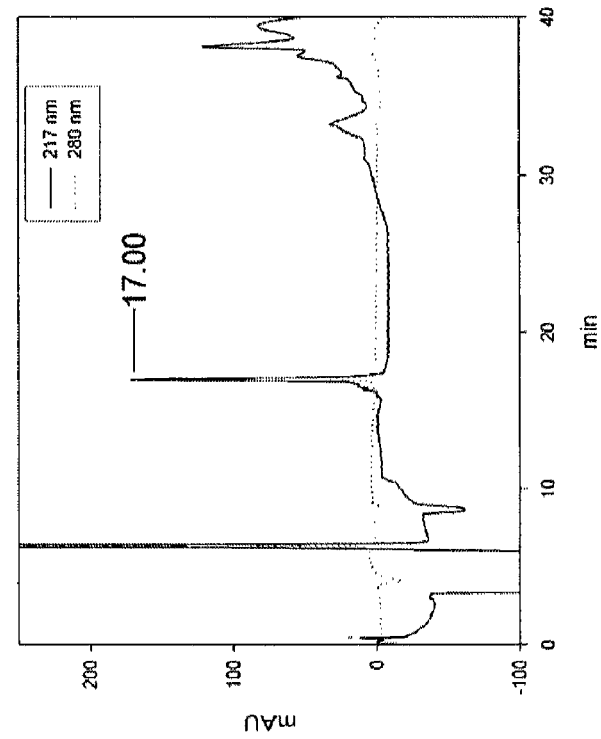
Figure 13:
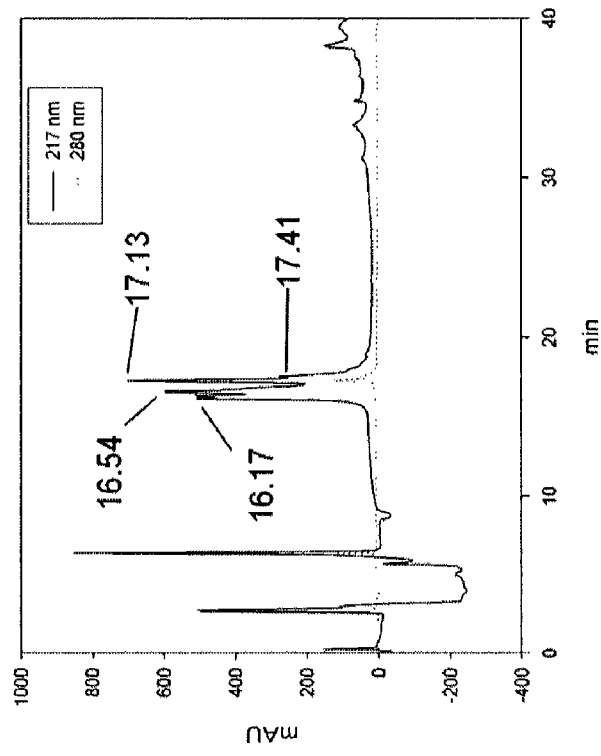

FIG. 13: depicts a RP-HPLC analysis of the reaction of cycloMcoEeTI hydrazide with sodium periodate after 10 min incubation (A) and a RP-HPLC analysis of the cyclic product eluting at 17 min (B).

THE FOLLOWING EXAMPLES ILLUSTRATE THE INVENTION

Example 1

Production and Assaying of TPO Agonists and Antagonists

Materials and Methods
Molecular Biological Techniques

Unless stated otherwise in the Examples, all recombinant DNA techniques are performed according to protocols as described in Sambrook and Russell (2001), Molecular Cloning: A Laboratory Manual, CSH Press, Cold Spring Harbor, N.Y., USA or in Volumes 1 and 2 of Ausubel et al. (1994), Current Protocols in Molecular Biology, Current Protocols.
DNA Constructs Construction of fusion genes consisting of an enzymatically inactive variant of *B. amyloliquefaciens* RNAse, barnase', and the coding sequence for the respective microprotein was done essentially as described. Microprotein genes were assembled in expression vector pBar100 (FIG. 2, EP 04 02 2455.2) by polymerase chain reaction using standard cloning methods (Sambrook et al., 2001). The ET-TP-020 encoding gene was assembled in a two step SOE PCR using the plasmid pBar100-EETI-II M71 (Schmoldt et al., 2004) as a template and the oligonucleotide pairs barmitte-up (5'CTTC-CGGGCAAAAGCGGACGAAC 3'; SEQ ID NO: 10) and ETTP21-SOE1lo (5'CAGCCAGCCACTGACGCAGGG-TCGGACCTTCGATGCACCCCATGGAAGAGCTTC 3; SEQ ID NO: 11) and ETTP21-SOE2up-new (5'CCTGCGT-CAGTGGCT GGCTGCTCGTGCTTGCAAA-CAG-GACTCCGACTG 3'; SEQ ID NO: 12) and cathindmitte-lo (5'CCACAA-GCTTGAAAACGTTTCAG 3'; SEQ ID NO: 13) with Taq DNA-Polymerase (NEB). Resulting products were purified by gel-electrophoresis and subsequent gel-extraction using the QIAquick Gel Extraction kit (Quiagen). They were then taken as a template for a second PCR reaction with the flanking oligonucleotides barmitte-up and cathindmitte-lo. The product was purified by phenol/chloroform extraction and ethanol precipitation, cleaved with Nco I and Hind III and ligated into similarly digested pBar100-EETI-II M71.
Protein Expression and Dimerization Fusion proteins were expressed and purified as described. The respective microprotein was released from the fusion partner barnase' by treatment with cyanogen bromide. The microprotein was purified by reversed phase HPLC as described (Schmoldt et al., 2004 and EP 04 02 2455.2).

To obtain the dimeric variants, 2 equivalents of the respective microprotein were dissolved in DMF/DMSO (1:1). Triethylamine was added at a final concentration of 1% together with 1 eq DSS (bis-succinimidyl suberate, Pierce), a bifunctional crosslinker. After overnight incubation the resulting dimeric crosslinked microprotein was purified by RP-HPLC.
Ba/F3 Reporter Cell Assay The expression vector for the TPOR/4Rα hybrid receptor, pcDNATPOR/4Rα, was constructed as follows. A PCR reaction was performed on a cDNA clone containing the human TPO receptor coding sequence using oligonucleotides TpoR-Xho-lo (5'-GCGCGCCTCGAGCCAGGCGGTCTCGGTG-GCGGTCTC-3'; SEQ ID NO.: 18) and TpoR-Xho-up (5'-GCGCGCCTCGAGCAAGATGTCTCCTTGCTGGCATC-3'; SEQ ID No.: 19). The resulting PCR product was digested with XhoI and ligated into similarly digested vector pASKcDNA-NH to yield pASKcDNA-NH-TPOR. pASKcDNA-NH resulted from the subcloning of an NheI/HindIII fragment of pcDNA/4Rα (Krause et al., 2004) in pASK21TETIsendc1/2 (Christmann et al., 1999). From the vector pASKcDNA-NH-TPOR the NheI/HindIII fragment containing the TPOR coding sequence was ligated to similarly digested pcDNA/4Rα to yield pcDNATPOR/4Rα. The STAT6 reporter gene construct pIeTATALuc was generated by insertion of a synthetic Hind III/Bam HI fragment representing the entire promoter/enhancer-sequence from the IL-4 responsive region of the human Iε promoter (Ezernieks et al., 1996) into luciferase expression plasmid pTATALuc+ (Altschmied et al., 1997).

Cell Culture, Transfection and Reporter Gene Assay

The murine pre-B cell line Ba/F3 was cultured as described (Lischke et al., 1995). Cells were transfected using the cell line Nucleofector™ kit V (Amaxa, Germany). Briefly, $8 \times 10^6$ cells were starved for 2 h in RPMI 1640/10% FCS, centrifuged and resuspended in 100 µl of transfection reagent V supplemented with 4 µg of expression vector pcDNATPOR/4Rα and 1 µg of reporter gene construct pIεTATALuc. Transfection was performed with the Nucleofector™ device applying program T16. Each transfection batch was recovered in 3.5 ml RPMI 1640/10% FCS and seeded at $2 \times 10^5$ cells/100 µl per well in a 96-well cell culture plate. Cells were left untreated for 1 h and then supplemented with various concentrations of hTPO (Immunotools, Germany) and individual microprotein candidates, respectively, to a total volume of 200 µl. For TPO competition assays cell aliquots were preincubated with individual microprotein samples 1 hour before stimulation with hTPO. After incubation for 12 h at 37° C., 5% $CO_2$, cell lysates were prepared and luciferase activity was measured as described previously (Krause et al., 2004).

Results

Table 1 shows the amino acid sequences of microproteins, into which the TpoR binding sequence (depicted in small letters) has been grafted. As microprotein scaffolds the microprotein AGRP', the melanocortin receptor binding domain of human agouti related protein (Mc Nulty et al., 2001) and the microprotein EETI-II (Christmann et al., 1999), respectively, were used. Underlined amino acids have been introduced as a spacer sequence or, as in SE-AG-TP-050, deviate from the sequence of the TPOR binding peptide. For determination of antagonist activity, the microproteins were used as fusion protein to barnase' (FIG. 2 and EP 04 02 2455.2). For determination of agonistic activity, the pure microproteins were used as dimers.

construct pIϵTATALuc (Krause et al., 2004). Inhibition of TPO receptor activation was measured using 5 nM TPO and 500 nM of each compound given in Table 1. As a result, the linear peptide (SN-LN-TP-020) as well as the microproteins SE-AG-TP-030, SE-AG-TP-040, SE-ET-TP-020 and SE-ET-TP-030 were able to act as TPO antagonists with respect to effective TPO mediated receptor activation. The same result was obtained for SE-AG-TP-040 in some assays. On the other hand, agonistic activity was shown for all the microproteins so far tested (Table 1).

FIG. 4 shows the agonistic action of SE-ET-TP-020. The SE-ET-TP020 microprotein was dimerized using the bifunctional chemical linker DSS. The purified dimer was used in the Ba/F3 TPO receptor activation assay in comparison with recombinant human TPO. FIG. 4 shows the activation of TPOR by human TPO in comparison with the activation by dimeric SE-ET-TP-020. The results show that dimeric SE-ET-TP-020 was active in the same dose range as TPO.

In the same manner, dimeric SE-AG-TP-040 and SE-AG-TP-050 were provided and tested for TPO agonistic activity. They are depicted in FIG. 5. The results indicated that these microprotein dimers efficiently activated the hybrid TPO receptor.

To assess the effect of the dimeric SE-ET-TP020 (also called: "SE-ET-TP-020d") on marrow cell proliferation, primary human marrow cells were cultured in semi-solid medium containing either no factors, 50 ng/ml or 10 ng/ml rhuTPO, or 30 nM, 10 nM or 3 nM dimeric SE-ET-TP-020d. After 10 to 12 days in culture, colonies of large cells (presumed to be megakaryocytes) were counted. The results are shown in FIG. 6. These results indicate that the dimeric microprotein SE-ET-TP-020d mimics TPO in its ability to stimulate the expansion of the Mk precursor cell population

TABLE 1

Amino acid sequences of microproteins with loop replacement by the thrombopoietin receptor (TPOR) binding sequence.

| Name | Sequence | Antagonist | Agonist EC50[nM] |
|---|---|---|---|
| SE-AG-TP-030 | GCVRLHESCLGQQVPCCDPAATCiegptlrqwlaaraCKGS (SEQ ID NO: 1) | + | nd. |
| SE-AG-TP-040 | GCVRLHESCLGQQVPCCDPAATC<u>GGTALA</u>iegptlrqwlaaraCKGS (SEQ ID NO: 2) | +− | ca 2 |
| SE-AG-TP-050 | GCVRLHESCLGQQVPCCDPAATC<u>GGTCLA</u>iegptlrqwl<u>C</u>araCKGS (SEQ ID NO: 3) | − | 2.5 |
| SE-AG-TP-060 | GCVRLHESCLGQQVPCCDPAATCYCiegptlrqwlaaCYCKGS (SEQ ID NO: 4) | − | n.d. |
| SE-ET-TP-020 | GCiegptlrqwlaaraCKQDSDCLAGCVCGPNGFCGS (SEQ ID NO: 5) | + | 1.4 |
| SE-ET-TP-030 | GCiegptlrqwlaaCKQDSDCLAGCVCGPNGFCGS (SEQ ID NO: 6) | + | 2.5 |
| SE-LN-TP-020 | iegptlrqwlaara (SEQ ID NO: 7) | + | n.d. |

Proteins were produced as fusion proteins with an enzymatically inactive barnase (barnase') and tested for their ability to block or induce hTPO receptor activation (antagonistic action). The microproteins tested for agonistic activity had been chemically dimerized. The test applied involved determining the ability to induce dimerization of TPOR extracelluar domains. n.d.: not determined.

FIG. 3 shows the results of a reporter gene assay using the murine hematopoietic progenitor cell line Ba/F3. These cells were transfected with a gene encoding a fusion of the hTPOR extracellular domain and the intracellular 4Rα domain from human 114-receptor and co-transfected with a reporter gene To assess the in vivo function of SE-ET-TP-020, Balb/c mice (n=5) were treated twice daily with 10 and 1000 μg/kg, respectively, SE-ET-TP-020 by subcutaneous injection. After 5 days, platelet count was measured in comparison to corresponding placebo experiments. As can be seen from FIG. 7, the treatment of mice with SE-ET-TP020 resulted in a doubling of the platelet count.

Example 2

Postsynthetic Cyclization of a Microprotein

Experimental Procedures
Abbreviations

Boc: tert.-butoxycarbonyl; DTT: ditiotreitol; ESI-MS: electrospray ionisation mass spectrometry; Fmoc: 9-fluorenylmethyloxycarbonyl; HATU: 2-(1H-9-azabenzotriazole-1-yl)-1,3,3,3-tetramethyluronium hexafluorophosphate; HBTU: 2-(1H-benzotriazole-1-yl)-1,3,3,3-tetramethyluronium hexafluorophosphate; HOBt: 1-hydroxy-1H-benzotriazole; HPLC: high pressure liquid chromatography; SPPS: solid phase peptide synthesis; TFA: trifluoroacetic acid.

Material

Reagents and solvents were of highest quality commercially available and were used without further purification. Sodium cyanoborohydride and sodium m-periodate were purchased from SIGMA-Aldrich, hydrazine monohydrate and cyanogen bromide from Fluka (Taufkirchen, Germany). ESI mass spectra were measured with a TSQ 700 Finnegan spectrometer. HPLC was performed on a Pharmacia Acta basis system using YMC J'sphere ODS H-80, RP C-18 columns for preparative runs (250×4.6 mm, 4 µm, 80 Å) and for the analytical samples (250×4.6 µm, 80 Å).

Construction of Expression Vector pBar100-cycloMcoEeTI

For generation of expression vector pBar100cycloMcoEeTI, the McoEeTI coding sequence was amplified in a two-step SOE-PCR with Taq Polymerase (Eppendorf). The initial PCR was done using the plasmid pBar100-McoEeTI (FIG. 2; EP 04 02 2455.2; Schmoldt et al., 2004) as a template and the oligonucleotides BspHI-McoTI-MSDGG-up (5'CGACCGGTCATGAGTGACGGTGGTGT TTGCCCGAAAAT 3'; SEQ ID NO: 14) and MCoTI-MS-DGGhinten-SOE-lo (5'CTTAACCACCGTCGGACA TGGACCCGCAGAAACCGTTG 3'; SEQ ID NO: 15) and MCoTI-MSDGGhinten-SOE-up (5'CCATGTCCGA CGGTGGTTAAGGGCCCAACGGTTTCTG 3'; SEQ ID NO: 16) and cat-hind-Mitte-lo (5'CCACAAGCT TGAAAACGTTTCAG 3'; SEQ ID NO: 17), respectively, to give two overlapping fragments. These fragments were used as templates for a second PCR with the flanking oligonucleotides BspHI-McoTl-MSDGG-up and cat-hind-Mitte-lo. The generated product was digested with Pag I and Hind III (MBI Fermentas) and ligated with pBar100-EETI-II M71 (Schmoldt et al., 2004) that had been cleaved with Nco I and Hind III to give expression vector pBar100-cycloMcoEeTI. This plasmid harbours a gene fusion of barnase', which is an inactivated mutant of the *Bacillus amyloliquefaciens* RNase barnase that is used as a purification handle, a phoA periplasmic leader sequence and the cycloMcoEeTI gene under tac promotor control. The resulting barnase'-cycloMcoEeTI fusion protein possesses two methionine residues—at the junction of barnase' and cycloMcoEeTI and at the C-terminus of cycloMcoEeTI—which can be cleaved with cyanogen bromide to remove the fusion partner barnase' and to generate a cycloMcoEeTI peptide with an N-terminal serine and a C-terminal homoserine-lactone (see e.g. FIG. 10 a, b).

Production and Purification of the Barnase'-cycloMcoEeTI Fusion

*E. coli* strain 71-18 [F' lacI$^q$ lacZΔM15 proA$^+$B$^+$ Δlac-proAB supE thi1] (source B. Müller-Hill) containing helper plasmid pRep4 (Qiagen) which contains a lacI gene was transformed with pBar100-cycloMcoEeTI by electroporation and grown overnight at 37° C. in 50 ml rich media containing 25 µg/ml chloramphenicol and 37.5 µg/ml kanamycin. Production was carried out in a 5 l fermenter (Bioengineering) as described (Schmoldt et al., 2004) and purification was done with slight modifications as described in Schmoldt et al. using barnase' as a purification handle. Briefly, the barnase'-cycloMcoEeTI fusion protein was purified from the culture medium after acidification with 55 ml of glacial acetic acid per liter of cell culture. The medium was filtered, diluted 1:5 with $H_2O$ and applied to a 100 mm diameter glass column containing 600 ml SP-Sepharose XL (Amersham Biosciences). The barnase'-fusion protein was eluted with a step gradient of 100 to 1000 mM NaCl and the fractions containing the fusion protein were directly applied to a 26 mm glass column containing 130 ml Amberchrom CG-300M (Tosoh Bioscience). After washing with $H_2O$/0.1% (v/v) acetic acid, the fusion protein was eluted from the column using a gradient from 0% (v/v) to 90% isopropanol/0.1% (v/v) acidic acid. Fusion protein containing fractions ranging from approximately 25-40% (v/v) isopropanol were combined and lyophilized. After re-solubilization in 8 M urea and dialysis against 50 mM ammonium acetate another cation exchange chromatography was made with a XK26 column (2.6×20 cm, 100 ml bed volume) containing SP-Sepharose XL (Amersham Biosciences) mounted to a Vision BioCad workstation (PerSeptive Biosystems) at a flow rate of 8 ml/min. Elution was performed with a gradient ranging from 0 to 0.5 M NaCl. Fusion protein containing fractions were combined and the protein was precipitated by adding ¹⁄₁₀ volume of 37% HCl and centrifugation for 10 min at 4000 rpm in a Haereus Omnifuge 3L-R.

CNBr Cleavage of Barnase'-cycloMcoEeTI

Precipitated fusion protein was solubilized in 20 ml 0.2 M HCl/8M urea per milligram of protein and 1 µl of 5 M cyanogen bromide solution (Fluka) was added (Kaiser and Metzka, 1999). After overnight incubation the sample was directly applied to a XK26 column (Amersham Biosciences) containing Amberchrom CG-300M (Tosoh Bioscience, 100 ml bed volume). After washing with $H_2O$/0.1% (v/v) TFA, the cleaved cycloMcoEeTI peptide was separated from barnase' using a gradient from 5% (v/v) to 90% acetonitrile/0.1% (v/v) TFA. CycloMcoEeTI containing fractions ranging from approximately 20 to 30% (v/v) acetonitrile were combined and lyophilized. Additional purification was made on Pharmacia Äcta basis system using YMC J'sphere ODS H-80, RP C-18 preparative column to give 5 mg of pure McoEeTI-serine lactone.

McoEeTI Hydrazide Formation:

Hydrazine hydrate (7 µL, 140 µmol) was added to McoEeTI homoserine lactone (2, 4.7 mg, 1.4 µmol) solution in water (2 mL). The mixture was stirred for 1 h at room temperature. The reaction was controlled by analytical HPLC. After the peak of starting lactone disappeared, the reaction mixture was lyophilised to remove the excess of hydrazine. The dry residue after lyophilization was redissolved in water-acetonitrile mixture and purified by a preparative HPLC. Pure yield: 2.1 mg (44.3%). HPLC: $t_R$=.ESI MS (methanol) revealed the following: m/z 856.0 ($[M+4H]^{4+}$, 100), 1152.6 ($[M+3H]^{3+}$, 33), 692.2 ($[M+5H]^{5+}$, 27), 1728.6 ($[M+2H]^{2+}$, 5).

Periodate Oxidation and Cyclization.

McoEeTI hydrazide (1.6 mg, 0.46 µmol) was dissolved in phosphate buffer (1 mL, mmol, pH 7). NaIO$_4$ (1 mg, 4.6 µmol) was added as a solution in phosphate buffer (1 mL) at room temperature. After 5 min the reaction was terminated by HPLC injection. Monitoring was conducted at 215 and 280 nm (absorbance of a macrocycle). Pure yield was 1 mg (63.7%).

REFERENCES

Altschmied, J., Duschl, J. (1997) Set of optimized luciferase reporter gene plasmids compatible with widely used CAT vectors. Biotechniques 23: 436-438.

Basser, R. L., Rasko, J. E., Clarke, K., Cebon, J., Green, M. D., Grigg, A. P., Zalcberg, J., Cohen, B., O'Byrne, J., Menchaca, D. M., Fox, R. M, and Begley, C. G (1997). Randomized, blinded, placebo-controlled phase I trial of pegylated recombinant human megakaryocyte growth and development factor with filgrastim after dose-intensive chemotherapy in patients with advanced cancer. Blood 89: 3118-3128.

Chase, T. & Shaw, E. (1970) in Meth. Enzymol. Vol. XIX (Perlman et al., eds), pp 20-27

Christmann, A., Walter, K., Wentzel, A., Kratzner, R., Kolmar H. (1999) The cystine knot of a squash-type protease inhibitor as a structural scaffold for *Escherichia coli* cell surface display of conformationally constrained peptides. Protein Eng 12(9):797-806.

Colgrave, M. L., and Craik, D. J. (2004) Thermal, chemical, and enzymatic stability of the cyclotide kalata B1: the importance of the cyclic cystine knot. Biochemistry 43: 5965-5975.

Craik, D. J., Daly, N. L., Bond, T., Waine, C. (1999) Plant cyclotides: A unique family of cyclic and knotted proteins that defines the cyclic cystine knot structural motif. J Mol. Biol. 294: 1327-1336.

Craik, D. J., Simonsen, S., Daly, N. L. (2002) The cyclotides: novel macrocyclic peptides as scaffolds in drug design. Curr Opin Drug Discov Devel. March; 5(2):251-60.

Craik, D. J., Daly, N. L., Mulvenna, J., Plan, M. R., and Trabi, M. (2004). Discovery, structure and biological activities of the cyclotides. Curr Protein Pept Sci. 2004 5:297-231

Craik, D. J., N. L. Daly, C. Waine, The cystine knot motif in toxins and implacations for drug design, Toxicon 39 (2001), 43-60

Cwirla, S. E., Balasubramanian, P., Duffin, D. J., Wagstrom, C. R., Gates, C. M., Singer, S. C., Davis, A. M., Tansik, R. L., Mattheakis, L. C., Boytos, C. M., Schatz, P. J., Baccanari, D. P., Wrighton, N. C., Barrett, R. W. and Dower W J. (1997) Peptide agonist of the thrombopoietin receptor as potent as the natural cytokine. Science 276:1696-1699.

Daly, N. L., Love, S., Alewood, P. F., and Craik, D. J. (1999) Chemical synthesis and folding pathways of large cyclic polypeptides: studies of the cystine knot polypeptide kalata B1. Biochemistry 38, 10606-10614

Daly, N. L., Gustafson, K. R., and Craik, D. J. (2004) The role of the cyclic peptide backbone in the anti-HIV activity of the cyclotide kalata B1. FEBS Lett. 574:69-72.

Davies, J. S. (2003) The cyclization of peptides and depsipeptides. J Pept Sci. 9: 471-501.

Dower, W. J, Cwirla, S. E., Balasubramanian, P., Schatz, P. J., Baccanari, D. P, Barrett, R. W. (1998) Peptide agonists of the thrombopoietin receptor. Stem Cells. Suppl 2:21-29.

Evans, T. C. Jr, Benner, J., and Xu, M. Q. (1999) The cyclization and polymerization of bacterially expressed proteins using modified self-splicing inteins. J Biol Chem 274: 18359-18363.

Ezernieks, J., Schnarr, B., Metz, K., and Duschl, A (1996) The human IgE germline promoter is regulated by interleukin-4, interleukin-13, interferon-alpha and interferon-gamma via an interferon-gamma-activated site and its flanking regions. Eur J. Biochem. 240: 667-673.

Fanucchi, M., Glaspy, J., Crawford, J., Garst, J., Figlin, R., Sheridan, W., Menchaca, D., Tomita, D., Ozer, H., and Harker, L. (1997). Effects of polyethylene glycol-conjugated recombinant human megakaryocyte growth and development factor on platelet counts after chemotherapy for lung cancer. N Engl J. Med. 336: 404-409.

Frank, S. J. (2002) Receptor dimerization in GH and erythropoietin action—it takes two to tango, but how? Endocrinology 143: 2-10.

Gaertner, H.F., Rose, K., Cotton, R., Timms, D., Camble, R. and Offord, R. E. (1992) Construction of protein analogues by site-specific condensation of unprotected fragments. Bioconjug Chem. 3: 262-268.

Geddis, A. E., Linden, H. M., and Kaushansky, K. (2002) Thrombopoietin: a pan-hematopoietic cytokine. Cytokine Growth Factor Rev.: 61-73.

Gelly, J. C., Gracy, J., Kaas, Q., Le-Nguyen, D., Heitz, A., Chiche, L. (2004) The KNOTTIN website and database: a new information system dedicated to the knottin scaffold. Nucleic Acids Res. January 1;32 Database issue:D156-9.

Geoghegan, K. F. and Stroh, J. G. (1992) Site-directed conjugation of nonpeptide groups to peptides and proteins via periodate oxidation of a 2-amino alcohol. Application to modification at N-terminal serine. Bioconjug Chem. 3:138-146.

Grotzinger, J. (2002) Molecular mechanisms of cytokine receptor activation. Biochim Biophys Acta. 1592: 215-223.

Gustafson, K. R., Sowder, R. C., II, Henderson, L. E., Parsons, I. C., Kashman, Y., Cardellina II, J. H., McMahon, J. B., Buckheit, R. W., Jr., Pannell, L. K., and Boyd, M. R. (1994) *J. Am. Chem. Soc.* 116, 9337-9338

Gustafson, K. R., Walton, L. K., Sowder, R. C. I., Johnson, D. G., Pannell, L. K., Cardellina, J. H. I., and Boyd, M. R. (2000) New circulin macrocyclic polypeptides from *Chassalia parvifolia* J. Nat. Prod. 63, 176-178

Hernandez, J. F., Gagnon, J., Chiche, L., Nguyen, T. M., Andrieu, J. P., Heitz, A., Trinh Hong, T., Pham, T. T., and Le Nguyen, D. (2000) Squash trypsin inhibitors from *Momordica cochinchinensis* exhibit an atypical macrocyclic structure. Biochemistry 39, 5722-30

Isaacs, N. W. (1995) Cystine knots. Curr. Biol. 5, 391-395

Iwai, H. and Pluckthun, A. (1999) Circular beta-lactamase: stability enhancement by cyclizing the backbone. FEBS Lett. 459:166-172.

Joseph, C. G., Bauzo, R. M., Xiang, Z., Shaw, A. M., Millard, W. J., Haskell-Luevano, C. (2003). Elongation studies of the human agouti-related protein (AGRP) core decapeptide (Yc[CRFFNAFC]Y) results in antagonism at the mouse melanocortin-3 receptor. Peptides 24: 263-270.

Kaiser, R. and Metzka, L. (1999) Enhancement of cyanogen bromide cleavage yields for methionyl-serine and methionyl-threonine peptide bonds. Anal Biochem. 266: 1-8.

Kaushansky, K., Lok, S., Holly, R. D., Broudy, V. C., Lin, N., Bailey, M. C., Forstrom, J. W., Buddle, M. M., Oort, P. J., Hagen, F. S, et al. (1994) Promotion of megakaryocyte progenitor expansion and differentiation by the c-Mpl ligand thrombopoietin. Nature 369:568-571.

Kohne, T., Kim, J. L., Kobayashi, K., Kodera, Y., Maeda, T., and Sato, K. (1995) Three-dimensional structure in solution of the calcium channel blocker omega-conotoxin MVIIA. Biochemistry 34:10256-10265.

Krause, S., Würdemann, D., Wentzel, A., Christmann, A., Fehr, H., Kolmar, H., and Friedrich K. (2004) Bacteria displaying interleukin-4 mutants stimulate mammalian cells and reflect the biological activities of variant soluble cytokines. Chembiochem 5: 804-810.

Kuter, D. J., Beeler, D. L. and Rosenberg, R. D. (1994) The purification of megapoietin: a physiological regulator of megakaryocyte growth and platelet production. Proc Natl Acad Sci USA.; 91:11104-11108.

Le-Nguyen, D., Heitz, A., Chiche, L., Castro, B., Boigegrain, R. A., Favel, A., and Coletti-Previero, M. A. (1990) Molecular recognition between serine proteases and new bioactive microproteins with a knotted structure Biochimie, 72 431-435

McNulty, J. C., Thompson, D. A., Bolin, K. A., Wilken, J., Barsh, G. S., and Millhauser, G. L. (2001) High-resolution NMR structure of the chemically-synthesized melanocortin receptor binding domain AGRP(87-132) of the agouti-related protein. Biochemistry 40: 15520-15527.

Lischke, A., Kammer, W., and Friedrich, K. (1995) Different human interleukin-4 mutants preferentially activate human or murine common receptor gamma chain. Eur Biochem 234:100-107.

Majerle, A., Kidric, J., and Jerala, R. (2000) Production of stable isotope enriched antimicrobial peptides in *Escherichia coli*: an application to the production of a 15N-enriched fragment of lactoferrin. J Biomol NMR 18: 145-151.

Mellado, M., Vila-Coro, A. J., Martinez, C., and Rodriguez-Frade, J. M (2001) Receptor dimerization: a key step in chemokine signalling. Cell Mol Biol (Noisy-le-grand). 47:575-582.

Metcalf, D. (1994) Thrombopoietin—at last. Nature 369: 519-520.

Miller, J. S., Westin, E. H., Schwartz, L. G. (1989) Cloning and characterization of complementary DNA for human tryptase J Clin Invest. October; 84(4): 1188-95.

Molina, M. A., Aviles, F. X., and Querol, E. (1992) Expression of a synthetic gene encoding potato carboxypeptidase inhibitor using a bacterial secretion vector. Gene 116:129-138.

Morrison, J. F., Kinetics of the reversible inhibition of enzyme-catalyzed reactions by tight-binding inhibitors, Biochim. Biophys. Acta 185 (1969) 269-286.

Muir, T. W. (2003) Semisynthesis of proteins by expressed protein ligation. Annu Rev Biochem 72: 249-289.

Newhouse, B. J., (2002) Tryptase inhibitors—review of the recent patent literature. IDrugs. 2002 July; 5(7): 682-8.

Pallaghy, P. K., Nielsen, K. J., Craik, D. J., and Norton, R. (1994) A common structural motif incorporating a cystine knot and a triple-stranded beta-sheet in toxic and inhibitory polypeptides. Protein Sci. 3, 1833-1839.

Price-Carter, M., Gray, W. R., and Goldenberg, D. P. (1996) Efficient disulfide-coupled folding of mature sequences in vitro. Biochemistry 35:15537-15546.

Rees, D. C, and Lipscomb W. N. (1983) Crystallographic studies on apocarboxypeptidase A and the complex with glycyl-L-tyrosine. Proc Natl Acad Sci U S A. 80:7151-7154.

Rose, K., Zeng, W., Regamey, P.O., Chernushevich, I. V., Standing, K. G. and Gaertner, H. F. (1996) Natural peptides as building blocks for the synthesis of large protein-like molecules with hydrazone and oxime linkages. Bioconjug Chem. 7: 552-556.

Saether, O., Craik, D. J., Campbell, I. D., Sletten, K., Juul, J., and Norman, D. G. (1995) Elucidation of the primary and three-dimensional structure of the uterotonic polypeptide kalata B1 Biochemistry 34, 4147-4158

Sambrook J., Fritsch E. F. & Maniatis T. (1989) Molecular cloning: a laboratory manual. pp. Pages. New York: Cold Spring Harbor Laboratory Press.

de Sauvage, F. J., Hass, P. E., Spencer, S. D., Malloy, B. E., Gurney, A. L., Spencer, S. A., Darbonne, W. C., Henzel, W. J., Wong, S. C., Kuang, W. J., et al. (1994) Stimulation of megakaryocytopoiesis and thrombopoiesis by the c-Mpl ligand. Nature. 369: 533-538.

Schmoldt, H.-U., Wentzel, A., Becker, S, and Kolmar, H. (2004) A fusion protein system for the recombinant production of short disulfide bond rich cystine knot peptides using barnase as a purification handle. Protein Exp Purif. in Press, Available online 2 Nov. 2004

Sommerhoff, C. P., Bode, W., Peireira, P. J., Stubbs, M. T., Sturzebecher, J., Piechottka, G. P., Matschiner, G., Bergner, A. (1999) The structure of the human betall-tryptase tetramer: fo(u)r better or worse. Proc Natl Acad Sci USA. September 28; 96(2): 10984-91, Scott, C. P., et al., (1999) Production of cyclic peptides and proteins in vivo. Proc Natl Acad Sci USA 96:13638-13643.

Tam, J. P. and Lu, Y. A. (1998) A biomimetic strategy in the synthesis and fragmentation of cyclic protein. Protein Sci 7: 1583-1592.

Tam, J. P., Lu, Y. A., Yang, J. L., and Chiu, K. W. (1999) An unusual structural motif of antimicrobial peptides containing end-to-end macrocycle and cystine-knot disulfides Proc. Natl. Acad. Sci. U.S.A. 96, 8913-8918

Trabi, M., Craik, D. J. (2002) Circular proteins—no end in sight. Trends Biochem Sci. 27:132-138.

Vanderslice, P., Ballinger, S. M., Tam, E. K., Goldstein, S. M., Craik, C. S., Caughey, G. H. (1990) Human mast cell tryptase: multiple cDNAs and genes reveal a multigene serine protease family. Proc Natl Acad Sci USA. 1990 May; 87(1): 3811-5.

Wendling, F., Maraskovsky, E., Debili, N., Florindo, C., Teepe, M., Titeux, M., Methia, N., Breton-Gorius, J., Cosman, D., and Vainchenker, W. (1994) cMpl ligand is a humoral regulator of megakaryocytopoiesis. Nature 369: 571-574.

Wentzel, A., Christmann, A., Kratzner, R., Kolmar, H. (1999) Sequence requirements of the GPNG beta-turn of the *Ecballium elaterium* trypsin inhibitor II explored by combinatorial library screening., J. Biol. Chem., 274, 21037-21043.

Williams, N. K., et al., (2002) In vivo protein cyclization promoted by a circularly permuted *Synechocystis* sp. PCC6803 DnaB mini-intein. J Biol Chem 277: 7790-7798.

The invention claimed is:

1. A polypeptide comprising at least two microproteins wherein the microproteins are linked by non-peptidic coupling, wherein the at least two microproteins comprise an amino acid sequence selected from the group consisting of an amino acid sequence depicted in any one of SEQ ID NOs: 1-6.

2. The polypeptide of claim 1 which is cyclic.

3. The polypeptide of claim 2 which forms a macrocycle, wherein the microproteins of said polypeptide are arranged so that the C-terminus of one microprotein is covalently bound to the N-terminus of another microprotein.

4. The polypeptide of claim 1, wherein said non-peptidic coupling comprises a bifunctional or oligofunctional linker molecule.

5. The polypeptide of claim 4, wherein said linker molecule is selected from the group consisting of adipinic acid hydrazide, bis-succinimidyl-suberate (DSS) and EDTA-hydrazide.

6. The polypeptide of claim 1, wherein said polypeptide has specific binding activity to a thrombopoietin (TPO) receptor.

7. The polypeptide of claim 6, wherein said polypeptide comprises the amino acid sequence IEGPTLRQWLAARA (SEQ ID NO: 7), which has binding activity to the TPO receptor.

8. A composition comprising the polypeptide of claim 1 and, optionally, a pharmaceutically acceptable carrier.

9. A kit comprising the polypeptide of claim 1.

10. A method for forming a polypeptide comprising at least two microproteins wherein the microproteins are linked by non-peptidic coupling and wherein the at least two microproteins comprise an amino acid sequence selected from the group consisting of SEQ ID NOs: 1-6 comprising:
(a) providing a microprotein substrate comprising an N-terminal reactive carbonyl group and a C-terminal homoserine lactone residue, and comprising an amino acid sequence selected from the group consisting of SEQ ID NOs: 1-6; and
(b) reacting the microprotein substrate so as to convert said N-terminal group and said C-terminal residue into a hydrazone linkage.

11. The method of claim 10, wherein the N-terminal reactive carbonyl group is a glyoxylyl group or a keto group.

12. The method of claim 11, wherein the glyoxylyl group is formed by mild oxidation of an N-terminal serine, threonine or hydroxylysine residue.

13. The method of claim 12, wherein the N-terminal serine or threonine residue of the microprotein substrate is provided by cleaving a precursor polypeptide comprising said microprotein substrate at the peptide bond between a methionine and a subsequent serine or threonine residue using cyanogen bromide.

14. The method of claim 10, wherein the C-terminal homoserine lactone residue of said microprotein substrate is provided by cleaving the peptide bond between a methionine and a subsequent amino acid residue using cyanogen bromide.

15. The method of claim 10, wherein step (b) comprises:
(i) reacting the C-terminal homoserine lactone residue to homoserine hydrazide;
(ii) reacting the homoserine hydrazide and the N-terminal reactive carbonyl group to generate a hydrazone; and
(iii) optionally reducing the hydrazone.

16. The method of claim 10, wherein step (b) is for generating a linear dimer or oligomer of said microproteins.

17. The method of claim 10, wherein step (b) is for generating a macrocyclic dimeric or oligomeric microprotein.

18. A polypeptide obtainable by the method of claim 10.

* * * * *

SEQUENCE LISTING

<160> NUMBER OF SEQ ID NOS: 20

<210> SEQ ID NO 1
<211> LENGTH: 41
<212> TYPE: PRT
<213> ORGANISM: Artificial Sequence

```
<220> FEATURE:
<223> OTHER INFORMATION: Description of Artificial Sequence: Synthetic
      recombinant microprotein

<400> SEQUENCE: 1

Gly Cys Val Arg Leu His Glu Ser Cys Leu Gly Gln Gln Val Pro Cys
1               5                   10                  15

Cys Asp Pro Ala Ala Thr Cys Ile Glu Gly Pro Thr Leu Arg Gln Trp
                20                  25                  30

Leu Ala Ala Arg Ala Cys Lys Gly Ser
        35                  40

<210> SEQ ID NO 2
<211> LENGTH: 47
<212> TYPE: PRT
<213> ORGANISM: Artificial Sequence
<220> FEATURE:
<223> OTHER INFORMATION: Description of Artificial Sequence: Synthetic
      recombinant microprotein

<400> SEQUENCE: 2

Gly Cys Val Arg Leu His Glu Ser Cys Leu Gly Gln Gln Val Pro Cys
1               5                   10                  15

Cys Asp Pro Ala Ala Thr Cys Gly Gly Thr Ala Leu Ala Ile Glu Gly
                20                  25                  30

Pro Thr Leu Arg Gln Trp Leu Ala Ala Arg Ala Cys Lys Gly Ser
            35                  40                  45

<210> SEQ ID NO 3
<211> LENGTH: 47
<212> TYPE: PRT
<213> ORGANISM: Artificial Sequence
<220> FEATURE:
<223> OTHER INFORMATION: Description of Artificial Sequence: Synthetic
      recombinant microprotein

<400> SEQUENCE: 3

Gly Cys Val Arg Leu His Glu Ser Cys Leu Gly Gln Gln Val Pro Cys
1               5                   10                  15

Cys Asp Pro Ala Ala Thr Cys Gly Gly Thr Cys Leu Ala Ile Glu Gly
                20                  25                  30

Pro Thr Leu Arg Gln Trp Leu Cys Ala Arg Ala Cys Lys Gly Ser
            35                  40                  45

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      recombinant microprotein

<400> SEQUENCE: 4

Gly Cys Val Arg Leu His Glu Ser Cys Leu Gly Gln Gln Val Pro Cys
1               5                   10                  15

Cys Asp Pro Ala Ala Thr Cys Tyr Cys Ile Glu Gly Pro Thr Leu Arg
                20                  25                  30

Gln Trp Leu Ala Ala Cys Tyr Cys Lys Gly
        35                  40

<210> SEQ ID NO 5
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      recombinant microprotein

<400> SEQUENCE: 5

Gly Cys Ile Glu Gly Pro Thr Leu Arg Gln Trp Leu Ala Ala Arg Ala
1               5                   10                  15

Cys Lys Gln Asp Ser Asp Cys Leu Ala Gly Cys Val Cys Gly Pro Asn
                20                  25                  30

Gly Phe Cys Gly Ser
            35

<210> SEQ ID NO 6
<211> LENGTH: 35
<212> TYPE: PRT
<213> ORGANISM: Artificial Sequence
<220> FEATURE:
<223> OTHER INFORMATION: Description of Artificial Sequence: Synthetic
      recombinant microprotein

<400> SEQUENCE: 6

Gly Cys Ile Glu Gly Pro Thr Leu Arg Gln Trp Leu Ala Ala Cys Lys
1               5                   10                  15

Gln Asp Ser Asp Cys Leu Ala Gly Cys Val Cys Gly Pro Asn Gly Phe
                20                  25                  30

Cys Gly Ser
        35

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      TPOR binding sequence

<400> SEQUENCE: 7

Ile Glu Gly Pro Thr Leu Arg Gln Trp Leu Ala Ala Arg Ala
1               5                   10

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(9)
<223> OTHER INFORMATION: Any amino acid
<220> FEATURE:
<221> NAME/KEY: MOD_RES
<222> LOCATION: (11)..(14)
<223> OTHER INFORMATION: Any amino acid
<220> FEATURE:
<221> NAME/KEY: MOD_RES
<222> LOCATION: (15)..(17)
<223> OTHER INFORMATION: Any amino acid or not present
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(24)
```

```
<223> OTHER INFORMATION: Any amino acid
<220> FEATURE:
<221> NAME/KEY: MOD_RES
<222> LOCATION: (25)..(25)
<223> OTHER INFORMATION: Any amino acid or not present
<220> FEATURE:
<221> NAME/KEY: MOD_RES
<222> LOCATION: (27)..(31)
<223> OTHER INFORMATION: Any amino acid
<220> FEATURE:
<221> NAME/KEY: MOD_RES
<222> LOCATION: (32)..(33)
<223> OTHER INFORMATION: Any amino acid or not present

<400> SEQUENCE: 8

Cys Xaa Xaa Xaa Cys Xaa Xaa Xaa Cys Xaa Xaa Xaa Xaa Xaa
1               5                   10                  15

Xaa Cys Xaa Cys Xaa Xaa Xaa Xaa Xaa Cys Xaa Xaa Xaa Xaa Xaa
            20                  25                  30

Xaa

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      thrombin recognition sequence

<400> SEQUENCE: 9

Leu Val Pro Arg Gly Ser
1               5

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttccgggca aaagcggacg aac                                          23

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagccagcca ctgacgcagg gtcggacctt cgatgcaccc catggaagag cttc         54

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctgcgtcag tggctggctg ctcgtgcttg caaacaggac tccgactg               48

<210> SEQ ID NO 13
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccacaagctt gaaaacgttt cag                                              23

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaccggtca tgagtgacgg tggtgtttgc ccgaaaat                              38

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cttaaccacc gtcggacatg gacccgcaga aaccgttg                              38

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccatgtccga cggtggttaa gggcccaacg gtttctg                               37

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccacaagctt gaaaacgttt cag                                              23

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgcgcctcg agccaggcgg tctcggtggc ggtctc                                36

<210> SEQ ID NO 19
<211> LENGTH: 35
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 19
gcgcgcctcg agcaagatgt ctccttgctg gcatc                              35

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      partial microprotein

<400> SEQUENCE: 20

Cys Tyr Cys Arg Phe Phe Asn Ala Phe Cys Tyr Cys
1               5                   10
```